(12) United States Patent
Godec et al.

(10) Patent No.: US 9,678,079 B2
(45) Date of Patent: Jun. 13, 2017

(54) MICROFLUIDIC LAL-REACTIVE SUBSTANCES TESTING METHOD AND APPARATUS

(71) Applicant: GENERAL ELECTRIC COMPANY, Schenectady, NY (US)

(72) Inventors: Richard Douglas Godec, Boulder, CO (US); Paul Charles Melanson, Boulder, CO (US); Matthew Kaddeland Stonesmith, Boulder, CO (US); Yan Huang, Shanghai (CN); Vidyasankar Sundaresan, Trevose, PA (US); Hong Xu, Shanghai (CN); Ruiqing Li, Shanghai (CN); Shouquan Deng, Shanghai (CN)

(73) Assignee: GENERAL ELECTRIC COMPANY, Schenectady, NY (US)

(*) Notice: Subject to any disclaimer, the term of this patent is extended or adjusted under 35 U.S.C. 154(b) by 140 days.

(21) Appl. No.: 14/434,361

(22) PCT Filed: Oct. 7, 2013

(86) PCT No.: PCT/US2013/063625
§ 371 (c)(1),
(2) Date: Apr. 8, 2015

(87) PCT Pub. No.: WO2014/058750
PCT Pub. Date: Apr. 17, 2014

(65) Prior Publication Data
US 2015/0260719 A1    Sep. 17, 2015

Related U.S. Application Data

(60) Provisional application No. 61/710,990, filed on Oct. 8, 2012, provisional application No. 61/710,908, filed
(Continued)

(51) Int. Cl.
*G01N 33/579* (2006.01)
*B01L 3/00* (2006.01)

(52) U.S. Cl.
CPC .......... *G01N 33/579* (2013.01); *B01L 3/5027* (2013.01); *B01L 3/5085* (2013.01);
(Continued)

(58) Field of Classification Search
CPC ..... B01L 2200/0605; B01L 2200/0684; B01L 2300/021; B01L 2300/0816;
(Continued)

(56) References Cited

U.S. PATENT DOCUMENTS 3,971,186 A    7/1976    Havelka et al.
4,717,658 A    1/1988    Michaels
(Continued)

FOREIGN PATENT DOCUMENTS

CA    2156226 A1    2/1996
CA    2420682 A1    3/2002
(Continued)

OTHER PUBLICATIONS

PCT Search Report and Written Opinion issued in connection with corresponding Application No. PCT/US2013/63645 on Feb. 17, 2014.
(Continued)

*Primary Examiner* — Maureen Wallenhorst
(74) *Attorney, Agent, or Firm* — Wegman, Hessler & Vanderburg

(57)    ABSTRACT

A microfluidic testing cartridge for testing LAL-reactive substances in fluid samples is provided. The cartridge may include at least two (2) testing modules, wherein each testing module includes at least one inlet port for receiving one of the fluid samples, and at least four (4) testing channels in fluid communication with the inlet port. Each of the testing
(Continued)

channels may include a metering portion for metering an aliquot of the fluid sample, an analyzing portion, and a mixing portion, wherein a valve is positioned between the metering portion and the analyzing portion to selectively fluidly separate the metering portion from the analyzing portion. The cartridge is insertable into an optical reader which performs optical measurements of the fluid sample within each testing channel during a testing process.

24 Claims, 8 Drawing Sheets

Related U.S. Application Data on Oct. 8, 2012, provisional application No. 61/710,898, filed on Oct. 8, 2012, provisional application No. 61/710,903, filed on Oct. 8, 2012.

(52) U.S. Cl.
CPC .. *B01L 3/502715* (2013.01); *B01L 2200/0605* (2013.01); *B01L 2200/0684* (2013.01); *B01L 2300/021* (2013.01); *B01L 2300/087* (2013.01); *B01L 2300/0816* (2013.01); *B01L 2300/0829* (2013.01); *B01L 2300/0864* (2013.01); *B01L 2300/0867* (2013.01); *B01L 2300/16* (2013.01); *B01L 2400/0406* (2013.01); *B01L 2400/0409* (2013.01); *B01L 2400/049* (2013.01); *B01L 2400/0487* (2013.01); *B01L 2400/0622* (2013.01); *B01L 2400/0688* (2013.01); *B01L 2400/0694* (2013.01); *G01N 2400/10* (2013.01); *G01N 2400/50* (2013.01); *Y10T 436/2575* (2015.01)

(58) Field of Classification Search
CPC ..... B01L 2300/0829; B01L 2300/0864; B01L 2300/0867; B01L 2300/087; B01L 2300/16; B01L 2400/0406; B01L 2400/0409; B01L 2400/0487; B01L 2400/049; B01L 2400/0622; B01L 2400/0688; B01L 2400/0694; B01L 3/5027; B01L 3/502715; B01L 3/5085; G01N 2400/10; G01N 2400/50; G01N 33/48; G01N 33/579; Y10T 436/11; Y10T 436/11166; Y10T 436/112499; Y10T 436/13; Y10T 436/25; Y10T 436/25375; Y10T 436/2575
USPC .... 436/43, 45, 46, 56, 63, 71, 94, 164, 165, 436/172, 174, 177, 180; 422/400, 402, 422/403, 404, 412, 415, 417, 419, 64, 72, 422/81, 82.05, 82, 8, 82.09, 502, 503, 422/504, 506, 507, 537; 435/5, 29, 435/287.1, 287.3, 288.3, 288.7
See application file for complete search history.

(56) References Cited

U.S. PATENT DOCUMENTS

| | | | |
|---|---|---|---|
| 4,819,713 A | 4/1989 | Weisman | |
| 4,824,303 A | 4/1989 | Dinger | |
| 4,879,634 A | 11/1989 | Storrow et al. | |
| 4,909,752 A | 3/1990 | Hallum et al. | |
| 5,010,444 A | 4/1991 | Storrow et al. | |
| 5,071,013 A | 12/1991 | Peterson | |
| 5,220,485 A | 6/1993 | Chakrabarti | |
| 5,224,016 A | 6/1993 | Weisman et al. | |
| 5,550,030 A | 8/1996 | Tanaka et al. | |
| 5,571,683 A | 11/1996 | Nakajima et al. | |
| 5,726,404 A * | 3/1998 | Brody | B01L 3/502738 137/261 |
| 5,859,764 A | 1/1999 | Davis et al. | |
| 6,212,075 B1 | 4/2001 | Habing et al. | |
| 6,270,982 B1 | 8/2001 | Jordan et al. | |
| 6,285,564 B1 | 9/2001 | O'Brien | |
| 6,687,130 B2 | 2/2004 | Adams, Sr. et al. | |
| 6,900,019 B1 | 5/2005 | Horton | |
| 7,031,167 B1 | 4/2006 | Zagoory et al. | |
| 7,180,737 B2 | 2/2007 | Straub, Jr. et al. | |
| 7,322,843 B1 | 1/2008 | Lee et al. | |
| 7,349,221 B2 | 3/2008 | Yurko | |
| 7,807,448 B2 | 10/2010 | Glezer et al. | |
| 8,045,332 B2 | 10/2011 | Lee et al. | |
| 2002/0137218 A1 | 9/2002 | Mian et al. | |
| 2002/0185183 A1 | 12/2002 | O'Connor et al. | |
| 2004/0121450 A1 | 6/2004 | Pugia et al. | |
| 2004/0131450 A1 | 7/2004 | Yang | |
| 2005/0026239 A1 | 2/2005 | Castro et al. | |
| 2005/0048655 A1 | 3/2005 | Novitsky et al. | |
| 2005/0106066 A1 | 5/2005 | Saltsman et al. | |
| 2005/0170515 A1 | 8/2005 | Moore | |
| 2007/0231217 A1 | 10/2007 | Clinton et al. | |
| 2007/0253169 A1 | 11/2007 | Clawser | |
| 2008/0187445 A1 | 8/2008 | Gale et al. | |
| 2008/0190220 A1 | 8/2008 | Backes et al. | |
| 2008/0239690 A1 | 10/2008 | Harvey et al. | |
| 2009/0139578 A1 | 6/2009 | Kim et al. | |
| 2009/0311796 A1 | 12/2009 | Griss et al. | |
| 2010/0330597 A1 | 12/2010 | Tsuchiya | |
| 2011/0079094 A1 | 4/2011 | Gransee et al. | |
| 2011/0124132 A1 | 5/2011 | Kim et al. | |
| 2011/0143364 A1 | 6/2011 | Kim et al. | |
| 2011/0201049 A1 | 8/2011 | Wainwright et al. | |
| 2011/0261537 A1 | 10/2011 | Sporer et al. | |
| 2012/0244607 A1 | 9/2012 | Iwamoto et al. | |
| 2015/0060272 A1 * | 3/2015 | Blidner | B01L 3/502738 204/403.05 |

FOREIGN PATENT DOCUMENTS

| | | |
|---|---|---|
| CA | 2820483 A1 | 7/2007 |
| CA | 2732011 A1 | 2/2010 |
| CA | 2755276 A1 | 9/2010 |
| CN | 1208464 A | 2/1999 |
| CN | 101368967 A | 2/2009 |
| CN | 101387647 A | 3/2009 |
| CN | 101389960 A | 3/2009 |
| CN | 101529246 A | 9/2009 |
| CN | 102177439 A | 9/2011 |
| CN | 102441356 A | 5/2012 |
| EP | 0320154 A1 | 6/1989 |
| EP | 0649021 A1 | 4/1995 |
| EP | 0690308 A2 | 1/1996 |
| EP | 0921397 A1 | 6/1999 |
| EP | 0957366 A1 | 11/1999 |
| EP | 1983347 A2 | 10/2008 |
| JP | 6193958 A | 5/1986 |
| JP | 10253630 A | 9/1998 |
| JP | 2004212120 A | 7/2004 |
| WO | 9721090 A1 | 6/1997 |
| WO | 9943432 A1 | 9/1999 |
| WO | 2004065930 A2 | 8/2004 |
| WO | 2006070376 A1 | 7/2006 |
| WO | 2009005231 A1 | 1/2009 |
| WO | 2009105711 A1 | 8/2009 |
| WO | 2011096782 A2 | 8/2011 |

OTHER PUBLICATIONS

PCT Search Report and Written Opinion issued in connection with corresponding Application No. PCT/US2013/063649 on Apr. 30, 2014.

PCT Search Report and Written Opinion issued in connection with corresponding Application No. PCT/US2013/63639 on Jun. 25, 2014.

(56) References Cited

OTHER PUBLICATIONS

Baines, "Endotoxin Testing" In: Handbook of Microbiological Quality Control in Pharmaceuticals and Medical Devices, pp. 144-167, 2003.
Unoffcial English Translation of Chinese Office Action issued in connection with related CN Application No. 201380052528.7 on Oct. 27, 2015.
Unofficial English Translation of Chinese Office Action issued in connection with related CN Application No. 201380052524.9 on Dec. 4, 2015.
Hemker et al., "The Kinetics of Enzyme Cascade Systems General Kinetics of Enzyme Cascades," The Procedures of the Royal Society, B (Biological Sciences), vol. No. 173, pp. 411-420, 1969.
Bryant et al., "Endotoxin Contamination of Enzyme Conjugates Used in Enzyme-Linked Immunosorbent Assays", Journal of Clinical Microbiology, vol. No. 17, Issue No. 6, pp. 1050-1053, Jun. 1983.
Suh et al., "Feasibility of On-Chip Detection of Endotoxin by LAL Test", Biotechnology and Bioprocess Engineering, vol. No. 9, pp. 132-136, Jan. 1, 2004.
Mitsumoto et al., "Novel Endotoxin Assay by Laser Light-Scattering Particle-Counting Method", Journal of Clinical Laboratory Analysis, vol. No. 23, Issue No. 2, pp. 117-124, Jan. 1, 2009.
Cooper et al., "Automated Endotoxin Testing Program for High-Risk-Level Compounded Sterile Preparations at an Institutional Compounding Pharmacy", American Journal of Health-System Pharmacy: AJHP: Official Journal of the American Society of Health-System Pharmacists, vol. No. 67, Issue No. 4, pp. 280-286, Feb. 15, 2010.
The United States Pharmacopeia, "Bacterial Endotoxins Test", Biological Tests and Assays, USP Chapter 85, Reissue, pp. R65-R69, Oct. 1, 2010.
European Pharmacopoeia, "2.6.14 Bacterial Endotoxins", Seventh Edition, vol. No. 1, pp. 171-175, 2010.
Tsougeni et al., ""Smart" Polymeric Microfluidics Fabricated by Plasma Processing: Controlled Wetting, Capillary Filling and Hydrophobic Valving", The Royal Society of Chemistry, vol. No. 10, pp. 462-469, 2010.

Lonza, "Limulus Amebocyte Lysate (LAL) Kinetic-QCL", pp. 1-19, Jan. 1, 2011.
American National Standard, "Bacterial Endotoxins-Test Methods, Routine Monitoring, and Alternatives to Batch Testing", ANSI/AAMI ST72:2011, pp. 1-34, 2011.
The Japanese Pharmacopeia, "4.01 Bacterial Endotoxin Test", Sixteenth Edition, pp. 92-96, 2011.
Harwood, "3-Dimensional Compact Disc (CD) Microfluidic Platform", A Thesis, pp. 1-78, 2011.
ICH Harmonised Tripartite Guideline, "Evaluation and Recommendation of Pharmacopoeial Texts for Use in the ICH Regions on Bacterial Endotoxins Test General Chapter", Q4B Annex 14, Step 4 version, Oct. 18, 2012.
The United States Pharmacopeia, "Transfusion and Infusion Assemblies and Similar Medical Devices", USP Chapter 161, vol. No. 1, pp. 131-132, May 1, 2013.
PCT Search Report and Written Opinion issued in connection with corresponding Application No. PCT/US2013/038638 on Jan. 7, 2014.
PCT Search Report and Written Opinion issued in connection with corresponding Application No. PCT/US2013/063625 on Jan. 24, 2014.
Nichols et al., "LALreview", PryoSense®-PAT for WFI, Published by Lonza, Issue No. 1, pp. 1-6, 2008.
WinKQCL®4., "Endotoxin Detection and Analysis Software", Lonza, Copyright, pp. 1-11, Mar. 2009.
Gee et al., "A Multi-Center Comparison Study Between The Endosafe PTS(TM) Rapid Release Testing System and Traditional Test Methods for Detecting Endotoxin in Cell Theraphy Products", Cytotherapy, vol. No. 10, Issue No. 1, pp. 1-15, Aug. 22, 2008.
Lonza, "Endotoxin Detection: Products and Services", pp. 1-36, May 1, 2010.
PCT Invitation to Pay Additional Fees issued in connection with related WO Application No. PCT/US2013/063649 on Feb. 17, 2014.
Unofficial English Translation of Chinese Office Action issued in connection with related CN Application No. 201380052528.7 on Jul. 12, 2016.
US Non-Final Office Action issued in connection with Related U.S. Appl. No. 14/434,364 on Aug. 29, 2016.

\* cited by examiner

| Step | Port state | | | | Burst Valves | | | | Channel Pressure | | | Notes |
|---|---|---|---|---|---|---|---|---|---|---|---|---|
| | A | B | C | D | E | F | G | H | J | K | |
| 1 | Vent | Vent | Vent | 0.5 | 1.5 | 0.5 | 1.5 | 0 | 0 | 0 | Load sample |
| 2 | -1 | -1 | -1 | 0.5 | 1.5 | 0.5 | 1.5 | -1→0 | -1→0 | -1 | Loading for metering |
| 3 | -2 | Closed | Closed | 0.5 | 1.5 | 0.5 | 1.5 | 0 | 0 | -1 | Drawing off excess |
| 4 | Closed | Vent | -2 | 0.5 | 1.5 | 0.5 | 1.5 | 0 | 0 | -2→0 | Shuttle to end |
| 5 | Closed | -2 | Vent | Closed | 1.5 | 0.5 | 1.5 | -2 | -2 | 0 | Mix |
| 6 | Closed | Vent | -2 | Closed | 1.5 | 0.5 | 1.5 | 0 | 0 | -2→0 | Mix |
| 7 | Closed | Closed | Closed | Closed | 1.5 | 0.5 | 1.5 | 0 | 0 | 0 | Measure |

FIG. 4A

| Step | Port state | | | | Burst Valves | | | | Channel Pressure | | | Notes |
|---|---|---|---|---|---|---|---|---|---|---|---|---|
| | A | B | C | D | E | F | G | H | J | K | |
| 1 | Vent | Vent | Vent | 0.5 | 0.5 | 0.5 | 0.5 | 0 | 0 | 0 | Load sample |
| 2 | -1 | -1 | Closed | 0.5 | 0.5 | 0.5 | 0.5 | -1→0 | -1→0 | -0.1 | Loading for metering |
| 3 | -1 | Closed | Closed | 0.5 | 0.5 | 0.5 | 0.5 | 0 | 0 | -0.1 | Drawing off excess |
| 4 | Closed | Vent | -1 | 0.5 | 0.5 | 0.5 | 0.5 | 0 | 0 | -1→0 | Shuttle to end |
| 5 | Closed | -1 | Vent | Closed | 0.5 | 0.5 | 0.5 | -1 | -1 | 0 | Mix |
| 6 | Closed | Vent | -1 | Closed | 0.5 | 0.5 | 0.5 | 0 | 0 | -1→0 | Mix |
| 7 | Closed | Closed | Closed | Closed | 0.5 | 0.5 | 0.5 | 0 | 0 | 0 | Measure |

FIG. 4B

| Sample well | Sample | Optical well | Endo-toxin | Description |
|---|---|---|---|---|
| 1 | Lal reagent water | 1 | 0 | Negative control (blank) rep 1 |
|  |  | 2 | 0 | Negative control (blank) rep 2 |
|  |  | 3 | 0 | Negative control (blank) rep 3 |
|  |  | 4 | Lowest | Lowest detection range calibration standard rep 1 |
| 2 | Lal reagent water | 5 | Lowest | Lowest detection range calibration standard rep 2 |
|  |  | 6 | Lowest | Lowest detection range calibration standard rep 3 |
|  |  | 7 | Mid range | Mid range calibration standard rep 1 |
|  |  | 8 | Mid range | Mid range calibration standard rep 2 |
| 3 | Lal reagent water | 9 | Mid range | Mid range calibration standard rep 3 |
|  |  | 10 | Highest | Highest detection range calibration standard rep 1 |
|  |  | 11 | Highest | Highest detection range calibration standard rep 2 |
|  |  | 12 | Highest | Highest detection range calibration standard rep 3 |
| 4 | Sample A | 13 | 0 | Sample A analysis rep 1 |
|  |  | 14 | 0 | Sample A analysis rep 2 |
|  |  | 15 | Mid range | Positive control spike for sample A rep 1 |
|  |  | 16 | Mid range | Positive control spike for sample A rep 2 |
|  |  | ⋮ |  |  |
| 24 | Sample U | 93 | 0 | Sample U analysis rep 1 |
|  |  | 94 | 0 | Sample U analysis rep 2 |
|  |  | 95 | Mid range | Positive control spike for sample U rep 1 |
|  |  | 96 | Mid range | Positive control spike for sample U rep 2 |

Fig. 5A

| Sample well | Sample | Optical well | Endo-toxin | Description |
|---|---|---|---|---|
| 1 | Lal reagent water | 1 | 0 | Negative control (blank) rep 1 |
| | | 2 | 0 | Negative control (blank) rep 2 |
| | | 3 | 0 | Negative control (blank) rep 3 |
| | | 4 | Lowest | Lowest detection range calibration standard rep 1 |
| | | 5 | Lowest | Lowest detection range calibration standard rep 2 |
| | | 6 | Lowest | Lowest detection range calibration standard rep 3 |
| | | 7 | Mid range | Mid range calibration standard rep 1 |
| | | 8 | Mid range | Mid range calibration standard rep 2 |
| | | 9 | Mid range | Mid range calibration standard rep 3 |
| | | 10 | Highest | Highest detection range calibration standard rep 1 |
| | | 11 | Highest | Highest detection range calibration standard rep 2 |
| | | 12 | Highest | Highest detection range calibration standard rep 3 |
| 2 | Sample A | 13 | 0 | Sample A analysis rep 1 |
| | | 14 | 0 | Sample A analysis rep 2 |
| | | 15 | Mid range | Positive control spike for sample A rep 1 |
| | | 16 | Mid range | Positive control spike for sample A rep 2 |
| | | • • • | | |
| 22 | Sample U | 93 | 0 | Sample U analysis rep 1 |
| | | 94 | 0 | Sample U analysis rep 2 |
| | | 95 | Mid range | Positive control spike for sample U rep 1 |
| | | 96 | Mid range | Positive control spike for sample U rep 2 |

Fig. 5B

| Range | Lowest | Mid range | Highest |
|---|---|---|---|
| 0.005 - 0.5 | 0.005 | 0.05 | 0.5 |
| 0.01 - 1 | 0.01 | 0.1 | 1 |
| 0.05 - 5 | 0.05 | 0.5 | 5 |
| 0.1 - 10 | 0.1 | 1 | 10 |
| 0.5 - 50 | 0.5 | 5 | 50 |

MICROFLUIDIC LAL-REACTIVE SUBSTANCES TESTING METHOD AND APPARATUS

CROSS-REFERENCE TO RELATED APPLICATIONS

This is a national stage application under 35 U.S.C. §371(c) of prior-filed, co-pending, PCT application serial number PCT/US2013/063625, filed on Oct. 7, 2013, which claims priority to Provisional Patent Application Ser. No. 61/710,908 filed Oct. 8, 2012 and titled MICROFLUIDIC BACTERIA ENDOTOXIN TESTING METHOD AND APPARATUS; Provisional Patent Application Ser. No. 61/710,990 filed Oct. 8, 2012 and titled CENTRIPETAL MICROFLUIDIC PLATFORM FOR BACTERIAL ENDOTOXIN TESTING; Provisional Patent Application Ser. No. 61/710,898 filed Oct. 8, 2012 and titled SENSITIVE AND RAPID METHOD FOR DETECTION OF LOW LEVELS OF ENDOTOXINS USING LAL REAGENTS; and Provisional Patent Application Ser. No. 61/710,903 filed Oct. 8, 2012 and titled MICROPLATES PRELOADED WITH ENDOTOXIN DETECTION REAGENTS WITH CALIBRATION MEANS. All of the above listed applications are herein incorporated by reference.

FIELD OF THE INVENTION

Embodiments of the present invention direct to the field of determining the concentration of LAL-reactive substances in a fluid sample, and more particularly, embodiments of the present invention relate to semi-automated methods and apparatuses for measuring LAL-reactive substances in fluid samples.

BACKGROUND OF THE INVENTION

Microbial contamination, such as Gram positive bacteria, Gram negative bacteria, yeast, and fungi may cause severe illness and even death in humans. When people become infected with gram negative bacteria, the bacteria may produce fever-inducing bacterial endotoxins. Endotoxins can be dangerous and even deadly to humans. Endotoxin molecules, which are lipopolysaccharide components of cell walls of gram negative bacteria, can be present in drug formulations and surfaces of medical devices, independent of microbial contamination. Endotoxin contamination can happen even if a system passes a sterility test, which is why an independent endotoxin test is required.

Currently, a variety of tests have been developed to detect the presence of endotoxin in or on the sample being tested using hemocyte lysates from horseshoe crabs. Clotting will occur when the hemocyte lysate is exposed to the endotoxin. Hemocyte lysate is amebocyte lysate produced from the hemolymph of various horseshoe crab species, including the *Limulus, Tachypleus*, and *Carcinoscorpius* species. A commonly used amebocyte lysate is produced from the hemolymph of *Limulus*, or *Tachypleus* species, is referred to as *Limulus* amebocyte lysate ("LAL"). Routine tests that use LAL include gel clot assays, end point turbidometric assays, kinetic turbidometric assays, endpoint chromogenic assays, and kinetical chromogenic assays. Tests that use LAL may also be used to test for certain types of glucans, markers for fungal contamination.

More information on LAL assays and the standards used may be found in United States Pharmacopeia ("USP") Chapter 85 "Bacterial Endotoxins Test" ("BET"), Japanese Pharmacopeia 4.01 "Bacterial Endotoxin Test", European Pharmacopoeia 2.6.14 "Bacterial Endotoxins", and other equivalent national Pharmacopeias. Additional internationally harmonized pharmacopeia information can be found in ICH Q4B Annex 14 "Bacterial Endotoxin Test General Chapter". For endotoxin testing in medical devices, information can be found in USP Chapter 161 "Transfusion and Infusion Assemblies and Similar Medical Devices" and ANSI/AAMI ST72 "Bacterial endotoxins—Test methods, routine monitoring, and alternatives to batch testing". These standards and procedures may be generally referred to as compendia.

Manufacturers in the pharmaceutical, medical device and food industries must meet certain standards to make sure their products do not contain microbial or endotoxin contamination. These industries require frequent, accurate, and sensitive testing for the existence of endotoxins to meet various safety standards, such as those set by the United States Food and Drug Administration, or the Environmental Protection Agency. These agencies accept many of the compendia procedures standards. Thus, if manufacturers want to obtain government approval to release a new product to market, many of the FDA requirements may be met if the products comply with the methods and standards in the compendia listed above. This can substantially reduce the cost to manufacturers to obtain FDA approval of new products.

These agencies also have strict reporting requirements when test results show bad results, or endotoxin concentrations outside the expected range. Such non-compliant results must be thoroughly investigated to find the root cause and explained to the regulating agency. This is time consuming and costly. If manufacturers can show the non-compliant result occurs because of an anomaly in the test itself, and not because of the presence of an endotoxin actually in or on the sample, many of the reporting requirements to the agencies may be satisfied. This may reduce the time and cost incurred to fulfill such reporting obligations. To date, there are no known methods or apparatuses that are capable of distinguishing between anomalies or errors in the test itself and an anomaly in the sample.

These assays in the various compendia require aqueous solutions comprising known concentrations of an endotoxin for use as standards. These aqueous solutions are typically unstable; therefore they are usually made from powdered toxins at the test location just prior to testing. The LAL reagent also usually comes in powder form and must be reconstituted in an aqueous solution before use.

Preparation of the endotoxin and LAL powders is difficult due to the slow solvation of the critical biological molecules and their propensity to stick to surfaces during mixing and condense on surfaces afterwards. The LAL reagent also starts reacting slowly upon reconstitution and has a very short shelf life. While the best practice would be to mix these immediately before use, workflow typically dictates mixing them at the start of the process. Also, the process of preparation is prone to contamination from endotoxins which are ubiquitous in the environment.

The agencies also require a series of calibration tests to ensure the equipment and reagents used are functioning properly. The calibration tests and sample measurements must also be made more than once. The current laboratory method of complying with BET and other compendia is very detailed and requires repetitive and highly precise measuring of fluid volumes for distribution into multiple inlets of a microplate or the like without contamination.

The most common method of performing an LAL analysis is with a microwell plate and reader. A matrix of reaction wells, open at the top and with a clear window on the bottom, are placed in a heated spectrophotometric reader used for multiple, simultaneous assays. There are many drawbacks, including the lengthy time it takes to prepare the plate, its high cost, the opportunity for mistakes and contamination, and the need to have the work done by a technician specifically trained for and dedicated to this task.

Highly skilled operators are continuously monitored to ensure proper technique and accuracy of measurement and testing, and the operators are retrained as needed so as to ensure accuracy of the repetitive actions. Typical methods may have as many as 248 slow and time consuming pipetting steps, making it an error prone method due to its complexity and contamination prone due to its length and number of manipulations.

Methods and devices have been developed to reduce the amount of steps or automated some or all of the steps in endotoxin testing. Some methods include automating one or more pipetting or aliquoting steps, automated mixing of samples, or preloading reagents in test substrates that allow only a very limited number of tests. All of the developed methods or devices, however, are missing one or more of the following aspects, low cost automation designed into the substrate, disposable clean substrate to insure cleanliness, compendial testing compliance on each substrate, built in individual test measurement validation, and simplicity of measurement operation.

Other microfluidic methods exist to partially automate the assay process, but these are not fully compatible with the compendia methods due to their limited size and their reliance on a stored calibration rather than on calibrations run at the same time in the same apparatus using the same reagents and standards. It also requires a precise sample measurement; no aliquots are generated by the instrument or apparatus itself.

Other automated methods rely on robotics to measure and distribute samples and reagents in a microplate. Once prepared, the plate is loaded in a reader, either manually or using another robot. The robot is typically a pipette-based dispensing system which accurately transfers samples and reagents from a vial rack to the plate, replacing pipette tips to prevent cross-contamination. This is an expensive system which needs frequent validation of its robotic operations and multiple disposables (pipette tips, multiwall plates, dilution tubes, pipette filling trays, sampling vials, etc.) for each run. It also prepares the wells in sequence, and like manual preparation, cannot start all the reactions simultaneously. Contamination is still an issue and since the process is typically unmonitored, there is no legitimate way of rejecting contaminated samples for cause.

An automated system based on flow injection or sequential injection has also been developed. It uses disposable microfluidics which do not require cleaning and are not prone to contamination. This is a significant improvement in that it does analyses simultaneously and thus faster and as specified by compendia.

To date, however, there are no known methods or apparatuses that are capable of reducing the number steps the user has to perform in preparing and measuring both the calibration standards and measurement samples while complying with compendia Accordingly, there exists a need for a more semi-automated testing method or procedure for testing and analyzing the endotoxin concentration in a fluid sample which reduces or eliminates the amount of potential operator error and also complies with compendia.

BRIEF SUMMARY OF THE INVENTION

The present invention includes a microfluidic cartridge, systems and methods capable of performing LAL analyses, including multiple analyses for a single sample from a single source, analyses from this same source that have been "spiked" with additional endotoxin or glucan, standard concentrations of endotoxin or glucan, and blank water ("blank" or "LAL reagent water"). These analyses can be performed simultaneously in the same microfluidic cartridge or disposable device.

The present invention may be used to detect any LAL-reactive substance. As used herein LAL-reactive substance means a substance that reacts with an LAL reagent, including endotoxin or 1,3-β-D-glucans such as laminarin and curdlan. The present invention may also be used with any commercial source of LAL reagent or other reagents suitable for assaying LAL-reactive substances.

The present invention may reduce the number steps the user has to perform in preparing and measuring both the calibration standards and samples. This may reduce the need for a high level of skill, experience, and training, and reduces costs, times, and the opportunity for human error. The present invention may also be utilized to distinguish between anomalies or errors in the test itself and an anomaly in the sample. In addition embodiments of the invention may be configured or utilized in a manner that complies with compendia requirements and FDA regulations.

Embodiments of the invention are also suitable for use with all quantitative compendia photometric methods of relating the reaction progress to endotoxin levels, including 1) kinetic chromogenic, where the time until the optical absorption changes by a specified amount is related to concentration, 2) endpoint chromogenic, where the optical absorption change over a fixed time is related to concentration, 3) kinetic turbidimetric, where the time until the turbidity (usually measured by optical absorption) changes by a specified amount is related to concentration, and 4) endpoint turbidimetric, where the turbidity change over a fixed time is related to concentration. The cartridge enables the user to perform at least two simple or unadulterated analyses and at least two spiked analyses on each measurement sample, and at least two analyses of standards and blanks (calibration samples). This may be accomplished by having a sample introduction port in the cartridge for each fluid sample, a reservoir to hold the sample before processing, and a distribution means to at least four areas where samples may be precisely metered into exact volumes.

As used in this specification, the term "fluid sample" may include not only the sample to be analyzed ("measurement sample"), but water that shows no reaction with the endotoxin detection reagent or lysate employed at the detection limit. Samples of non-reactive water may also be referred to as "blanks", "LAL Reagent Water", "Water for BET" or "Water for Injection". The term "fluid sample" may also include solutions comprising a prepared solution comprising reagents, standards, spikes, or a prepared detection reagent. Reagent, as used herein, is used broadly and includes any substance chemical, or solution that is used the laboratory to detect, measure, otherwise examine substances, chemicals, or solutions, or aid in such examination. Reagent includes standards and detection reagents. Suitable detection reagents for LAL-reactive substances include LAL reagent, recombinant Factor C reagent, a mixture of recombinant Factor C and LAL reagent, and preparations that include sushi peptides, sushi peptide fragments, sushi peptide dimers, and other specific binding proteins such as antibodies and receptor binding proteins derived from bacteriophages. The term "fluid sample" may also include prepared solutions of endotoxin or glucan standard ("LAL-reactive substance" or "standard"). Each fluid sample type listed above may have its own introduction port or two or more of the fluid sample types may share at least one introduction port.

The cartridge enables the user to combine and mix metered samples and any reagents or standards that may be present. The cartridge may also have one or more optical chambers and may be inserted into an optical reader to measure optical changes in the fluid samples.

The cartridge may also contain similar structures for the analysis of blanks and standards that do not contain a fluidics network fluidics for the sample, so that a standard or blank and reagent are the fluids mixed and analyzed. At least three standards at different levels may be analyzed, with each standard and the blank having the means of being analyzed in at least three replicates from a single sample. Thus the cartridge supports analysis, in triplicate, of calibration standards at three different levels and a blank. The cartridge as described above allows for all the tests required by the compendia to be performed in one cartridge using the same sample.

In one embodiment, the measurement samples, reagents, and standards may all be introduced as prepared liquids ready for use. A single fluid sample of each type may be introduced to the disposable apparatus and then distributed.

In another embodiment, blank water may be used for the blank analysis and to distribute and dilute a single standard at the highest level. Thus, the standard is diluted as necessary by distribution, precise metering, and mixing to produce the other standards or spikes.

In yet another embodiment, the cartridge may be preloaded with standard, reagent, or mixtures thereof. The standards may be isolated in portions of the cartridge as a liquid or dried preparation that may be diluted or reconstituted. This eliminates the need for a standard introduction port. The isolated standards may be distributed or used directly in the mixing or analysis portions of the apparatus. For standard analyses, the standards are mixed with blank water and then distributed or used directly. For spikes, the standard may be reconstituted with sample, reagent, or a mixture of the two.

The reagent may also be isolated in the cartridge as a liquid or dried preparation, such that it may be diluted or reconstituted with blank water, and then distributed and used. This blank water may be sourced from the same reservoir as the analyzed blanks. The reagent may be isolated in each mixing area or other area unique to each analysis for reconstitution with blank water, sample, or both.

Alternatively, both the reagent and standards may be isolated in the cartridge. Thus, only samples and blank water need be added to the apparatus for analysis. It should also be noted that when the detection or LAL reagent is isolated in a dry form, it may be reconstituted with samples or standards instead of blank water, increasing the relative concentration of the material to be analyzed and increasing the speed and sensitivity of the assay.

The introduction ports, reservoirs, distribution means, analysis areas, metering means, and mixing means for all the analysis may be configured identically, such that the analyses, with the exception of any measurement samples, reagents or standards therein, are exact replicates of each other. The cartridge may be inserted in a reading apparatus. The reading apparatus may have all the necessary means of operating the cartridge. Operating means may include, but are not limited to, pumps, optics, temperature control, isolation from the environment, and combinations thereof. Alternatively, the operating means may be within the cartridge, or disposable cartridge. The reading apparatus may further comprise a computer with a memory, a processor, a user interface, and a means of displaying or reporting data. In one embodiment, the reading apparatus may be an optical reader.

The reading apparatus may also include a means of monitoring the process of the fluidics, especially fluidic metering and mixing. The reading apparatus may also have the means of validating the data by detecting abnormalities in the metering, mixing, or progress of the reaction so that abnormal analyses may be rejected.

One or more portions of the cartridge may have modified surfaces. The portions with modified surfaces may include, but are not limited to, channels, reservoirs, and optical chambers. The surfaces may be modified by any means known to those of ordinary skill in the art, including but not limited to, applying a coating, radiation, or dissolved reagents which may dynamically cover the surface, so that the interaction of the surfaces and reagents or samples mimic that of standard microplate analysis so that the manufacturer's specifications or compendia standards for analysis are met.

In one aspect of the present invention, a microfluidic cartridge for testing fluid samples is provided. The cartridge includes at least two testing modules, wherein each testing module includes an inlet port for receiving one of the fluid samples, and at least four testing channels in fluid communication with the inlet port. Each of the testing channels may include a metering portion for metering an aliquot of the fluid sample, an analyzing portion, and a mixing portion. The analyzing portion may be positioned between the metering portion and the mixing portion. A valve may be positioned between the metering portion and the analyzing portion to selectively fluidly separate the metering portion from the analyzing portion to allow precise and repeatable metering. Each testing module may have at least one testing channel with at least one reagent isolated therein.

In another embodiment, at least one testing module is a calibration module comprising at least eight (8) testing channels. At least two channels may have no LAL-reactive substance therein, at least 2 channels may have a first amount of a LAL reactive substance isolated therein, at least 2 channels may have a second amount of a LAL reactive substance isolated therein, and at least 2 channels may have a third amount of a LAL reactive substance isolated therein.

In yet another embodiment, at least one testing module is a sample measurement module comprising at least four (4) testing channels. At least two channels may have no LAL-reactive substance therein, and at least two channels may have a spike with a fourth amount of a LAL-reactive substance isolated therein.

In another embodiment, all of the testing channels may have at least one additional reagent isolated therein. The additional reagent may comprise a detection reagent. In another embodiment, the microfluidic cartridge may further comprise an exit port in fluid communication with the inlet port for removing excess of the fluid sample. This exit port can be internal and within the cartridge or an open port for fluid or pneumatic communications to the outside.

In yet another embodiment, the valve is configured to allow vacuum, centrifugal forces, or pneumatic pressure to motivate the aliquot across the valve to flow from the metering portion to the analyzing portion. In another embodiment, the microfluidic cartridge may further comprise a first pressure port positioned within the metering portion and adjacent to the end of the analyzing portion for creating a pressure differential within the testing channel. In yet another embodiment, the microfluidic cartridge may further comprise a second pressure port positioned within the mixing portion for creating a pressure differential within the testing channel.

In another embodiment, the analyzing portion may include an optical chamber to receive at least a portion of the aliquot for optical measurement of the fluid sample. In another embodiment, the mixing portion may be configured to allow the aliquot to mix with a reagent within the mixing portion. In yet another embodiment the reagent may be immobilized within the mixing portion.

In another aspect of the preset invention, a method for testing at least one fluid sample for LAL-reactive substances is provided. The method includes providing a microfluidic cartridge, wherein the cartridge includes at least two testing modules, wherein each testing module includes an inlet port for receiving one of the fluid samples, and at least four testing channels in fluid communication with the inlet port. Each of the testing channels may include a metering portion for metering an aliquot of the fluid sample, an analyzing portion, and a mixing portion. A valve may be positioned between the metering portion and the analyzing portion to selectively fluidly separate the metering portion from the analyzing portion. The method may further include introducing at least one fluid sample into at least one of the inlet ports. The method also includes introducing the microfluidic cartridge into an optical reader for optically measuring at least one fluid sample in the microfluidic cartridge. The method further includes performing a testing process on each of sample in the microfluidic cartridge and recording measurement data from the testing process.

In another embodiment, the method may further comprise motivating each of the aliquots from the metering portion to the analyzing portion for optical measurement in the analyzing portion of each testing channel. In yet another embodiment, a vacuum, centrifugal forces, or pneumatic pressure may motivate the flow of the aliquot across said valve from the metering portion to the analyzing portion. In another embodiment, each testing module may include at least one pressure port to which the vacuum or pneumatic pressure may be applied to create a pressure differential within the testing modules to motivate the flow of the aliquots.

In yet another method embodiment, the fluid sample may be introduced to the inlet ports manually or in an automated manner.

In another aspect of the preset invention, a method for testing at least one fluid sample for LAL-reactive substances is provided. The method includes providing a microfluidic cartridge, wherein the cartridge includes at least two testing modules, wherein each testing module includes an inlet port for receiving one of the fluid samples, and at least four testing channels in fluid communication with the inlet port. Each of the testing channels may include a metering portion for metering an aliquot of the fluid sample, an analyzing portion, and a mixing portion. A valve may be positioned between the metering portion and the analyzing portion to selectively fluidly separate the metering portion from the analyzing portion. The method may further include introducing at least one fluid sample into at least one of the inlet ports. The method further includes performing a testing process on each of sample in the microfluidic cartridge and recording measurement data from the testing process. In another method, the microfluidic cartridge may be introduced into an optical reader before introducing the fluid sample into an inlet port. In another method, the fluid sample may be mixed with a reagent during the testing process. In yet another embodiment, the reagent may be immobilized within the mixing portion.

In another aspect of the present invention, the measurement data may comprise aliquot volumes, reaction kinetics, fluid motions, transmission, absorption, optical density, color, color value, hue, spectrum, turbidity, scattered light, chemiluminescence, fluorescence, and magnetic resonance. The testing process and measurement data may be validated using historical measurement data and/or data from known reaction kinetics. In yet another embodiment, a tracer may be immobilized within the mixing portion and/or the analyzing portion to aid in measuring the aliquot volume.

Advantages of the present invention will become more apparent to those skilled in the art from the following description of the embodiments of the invention which have been shown and described by way of illustration. As will be realized, the invention is capable of other and different embodiments, and its details are capable of modification in various respects.

BRIEF DESCRIPTION OF SEVERAL VIEWS OF THE DRAWINGS

These and other features of the present invention, and their advantages, are illustrated specifically in embodiments of the invention now to be described, by way of example, with reference to the accompanying diagrammatic drawings, in which:

FIG. 4A is an exemplary diagram of a testing process for a testing module in a cartridge;

FIG. 4B is another exemplary diagram of a testing process for a testing module in a cartridge;

FIG. 5A is a chart of reagent/reactant within each testing channel of a cartridge;

FIG. 5B is an alternative chart of reagent/reactant within each testing channel of a cartridge;

Figure 1:
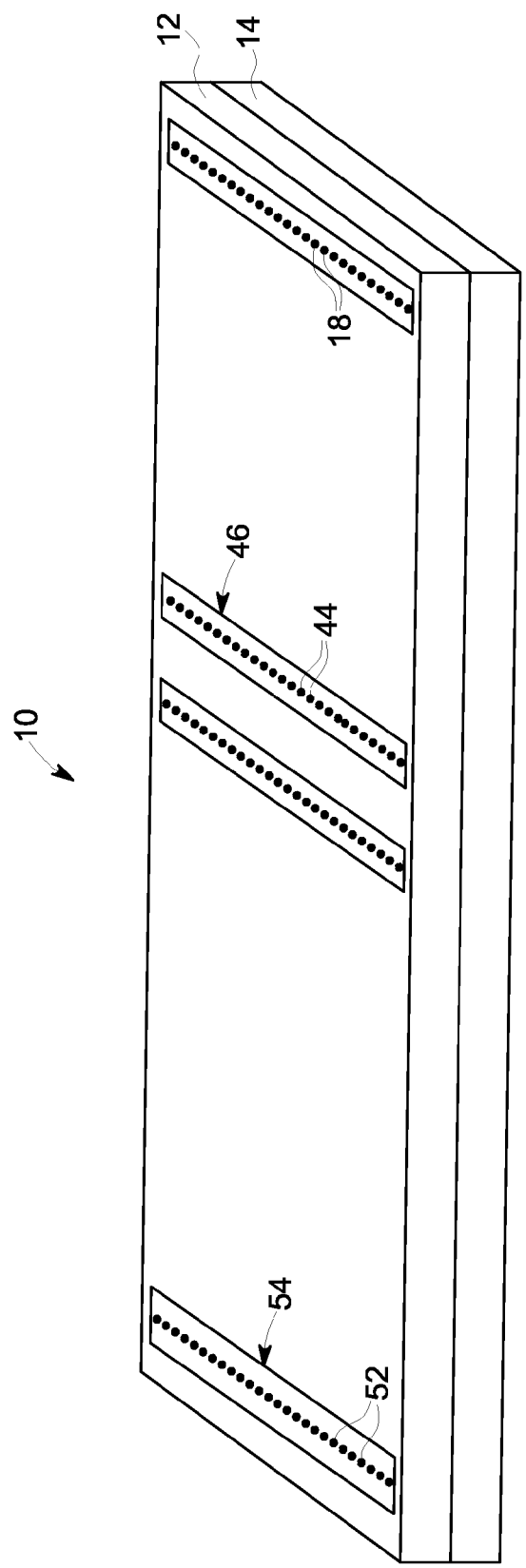
FIG. 1 is an exemplary embodiment of a cartridge for testing a plurality of fluid samples.

It should be noted that all the drawings are diagrammatic and not drawn to scale. Relative dimensions and proportions of parts of these figures have been shown exaggerated or reduced in size for the sake of clarity and convenience in the drawings. The same reference numbers are generally used to refer to corresponding or similar features in the different embodiments. Accordingly, the drawing(s) and description are to be regarded as illustrative in nature and not as restrictive.

DETAILED DESCRIPTION

Referring to FIG. 1, an exemplary embodiment of a membrane-based microfluidic LAL-reactive substance testing cartridge 10 for use in testing sample fluids is shown. The cartridge 10 improves the measurement of LAL-reactive substances within a fluid sample by improving the test accuracy, decreasing errors in measurement (timing, thermal variations, reaction initiation, reagent mixing, and optical measurements), decreasing sample contamination, increasing sample through-put, decreasing total test time, utilizing built-in test validations to increase reliability, and meeting all global regulatory agency and pharmacopeia requirements. The test for LAL-reactive substances is automated using the cartridge 10 which contains microfluidics and optical methods that allowing a high density of tests to be accomplished with a minimum amount of user input.

In an embodiment, the cartridge 10 is formed of an upper plate 12 and a lower plate 14, wherein the upper and lower plates 12, 14 are joined together and sealed by way of adhesive, ultrasonic welding, or otherwise fused together to form a unitary cartridge 10. At least a portion of a plurality of testing modules 16 is formed into each plate 12, 14 such that when the upper and lower plates 12, 14 are joined together, the testing modules 16 are sealed and defined. In another embodiment, the cartridge 10 is injection molded as a singular member such that the testing modules 16 are integrally formed therein. The cartridge 10 is formed of molded plastic, but can also be formed of any other material sufficient to provide for a plurality of testing pathways and being chemically inert with respect to the reagents and samples used during the testing procedures described below. In an embodiment, the cartridge 10 is formed of Polymethylmethacrylate (PMMA), Polystyrene, Cyclic Olefin Copolymer (COC), and Glycol-modified Polyethylene Terephtalate (PET-G), or any other moldable and substantially transparent polymer. In an embodiment, the cartridge 10 is formed by imprinting, hot-embossing, microcasting, injection molding, or the like.

In the exemplary embodiments shown in FIGS. 1-2, each cartridge 10 is configured to receive twenty-one (21) samples of fluid to be tested, in addition to a blank test as well as establishing a calibration curve, as provided in the United States Pharmacopeia ("USP") Chapter <85> Bacterial Endotoxins Test (hereinafter referred to as the "BET"), the standards of which are incorporated herein by reference. It should be understood by one of ordinary skill in the art that although the exemplary cartridge 10 shown and described herein includes twenty-four (24) testing modules 16 formed therein, other embodiments of cartridges 10 can be formed with more or fewer testing modules 16. It should also be understood by one of ordinary skill in the art that although the discussion below will be in reference to the use of the cartridge for carrying out the testing array provided in the BET, the cartridge 10 can also be configured to be used in any other testing method for testing fluid samples and providing a calibration test as well as a baseline blank test.

Figure 2:
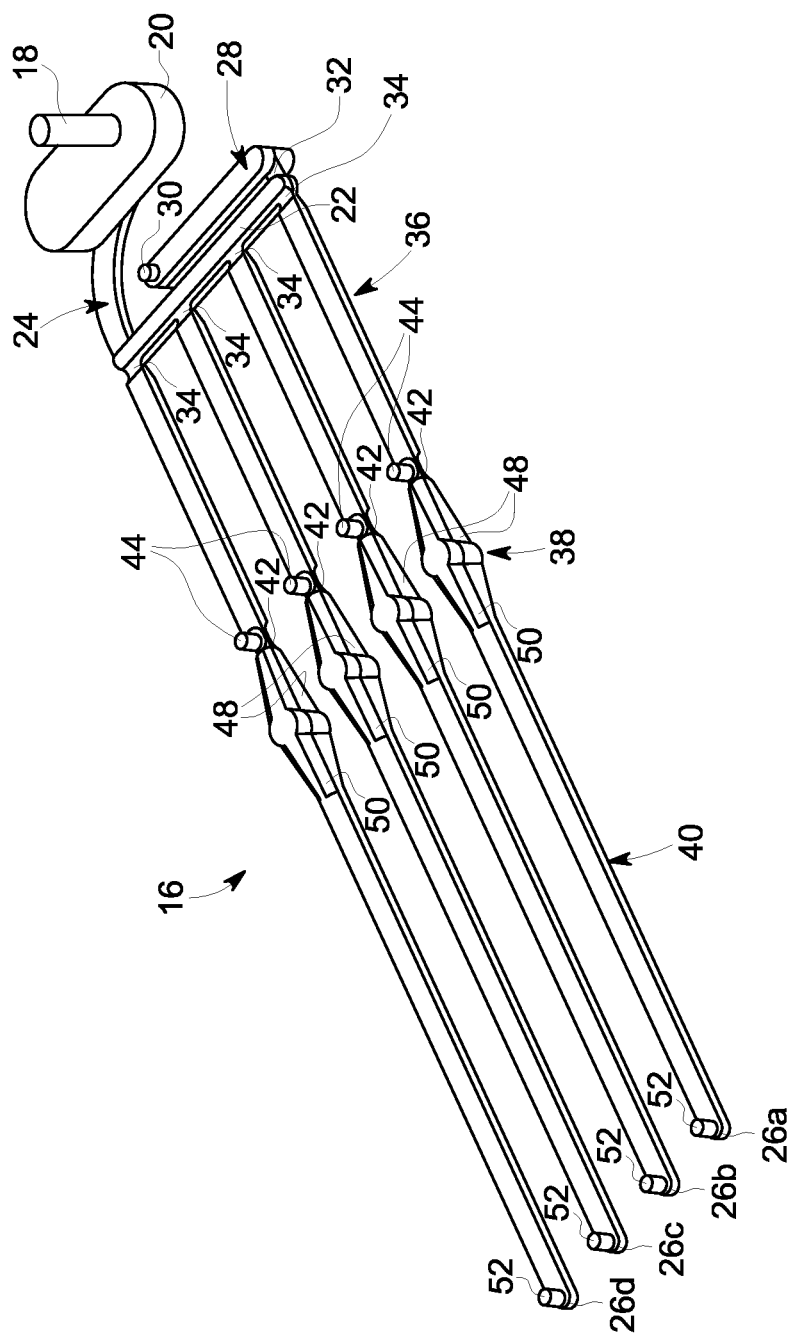
FIG. 2 is an exemplary embodiment of a testing module.

In an embodiment, each cartridge 10 includes a plurality of testing modules 16 formed therein, as shown in FIGS. 1-2. Each testing module 16 is a microfluidic device or element that is configured to accurately measure and test a fluid injected therein. The testing module 16 includes an inlet port 18 into which fluid is injected or otherwise introduced into the testing module 16. The fluid to be tested can be introduced into the inlet port 18 manually or in an automated manner. The inlet port 18 is fluidly connected to a reservoir 20 in which the fluid resides until the testing sequence is initiated. The fluid to be tested within each module 16 can be injected through the inlet port 18 by way of a pipette or any other injection apparatus that can accurately measure and deliver the measured volume of fluid. It should be understood by the description below that precise measurement of fluid to be introduced into each testing module 16 is not necessary, provided more fluid—and not less fluid—than necessary for testing is added to the reservoir 20. Once the fluid has been delivered through the inlet port 18, the fluid resides in the reservoir 20. In an embodiment, a pre-determined volume of fluid is introduced into the reservoir 20 for testing. In another embodiment, the reservoir 20 is completely filled with the fluid to be tested without precisely measuring the volume of fluid introduced into the inlet port 18.

As shown in FIG. 2, the reservoir 20 is fluidly connected to a first fluid manifold 22 by way of a transfer channel 24. The first fluid manifold 22 is an elongated hollow tube configured to distribute the fluid to each of the testing channels 26 as well as transfer excess fluid to be withdrawn from the exit port 30 to the exit channel 28. As the fluid is inserted into the reservoir 20, the fluid travels from the reservoir 20 and through the transfer channel 24 by any hydrostatic pressure of the fluid within the reservoir 20 due to its physical position and height, and any capillary pressure caused by the wetting of the walls of channel 24 by the sample, that cause the fluid to easily flow through the transfer channel 24 to the first fluid manifold 22. The first fluid manifold 22 is positioned substantially transverse relative to each of the testing channels 26, wherein an end of each testing channel 26 is in fluid communication with a different location along the length of the first fluid manifold 22. The transfer channel 24 is fluidly connected to, or adjacent to, a first distal end of the first fluid manifold 22, and the exit channel 28 is fluidly connected to, or adjacent to, an opposing second distal end of the first fluid manifold 22. The transfer channel 24 is directly connected to the first fluid manifold 22, and the exit channel 28 is connected to the first fluid manifold 22 by way of a first valve 32. The first valve 32 can be any valve that selectively allows the fluid to be transferred from the first fluid manifold 22 to the exit channel 28. The purpose of the valve is to aliquot a precise portion of one or more fluids for analysis.

In an embodiment, the first valve 32 is a burst valve. A burst valve changes in capillary pressures of the testing channels 26. This is done by controlling surface energy of fluidics and the size of channels. The burst valve can be used to prevent fluid from entering the analyzing portion 38 prematurely. In another embodiment, the first valve 32 can be formed as a passive valve generated by hydrophobic surface treatment utilizing plasma etching which manipulates the surface with wettability gradients adapted for microfluidic systems, as described in *"Smart" Polymeric Microfluidics Fabricated by Plasma Processing: Controlled Wetting, Capillary Filling and Hydrophobic Valving*, Katerina Tsougeni, et al. (Nov. 30, 2009), for example. It should be understood by one of ordinary skill in the art that the first valve 32 can be formed by surface treating the passageway between the exit channel 28 and the first fluid manifold 22 or by a physical barrier or membrane positioned within the passageway. In yet another embodiment, the first valve 32 is a mechanical valve that can be selectively actuated manually, electrically, or by way of pressure differential thereacross to allow fluid to flow between the first fluid manifold 22 and the exit channel 28. In one embodiment, the pressure differential may be created by applying centrifugal forces to the microfluidics cartridge. In another embodiment the valve can be a siphon valve designed for use in centripetal systems where a change in rotational speed activates the valve. In still a further embodiment, the first valve 32 is a membrane positioned within the passageway between the first fluid manifold 22 and the exit channel 28.

The first valve 32 is configured to be a hydrophobic porous barrier to selectively prevent fluid from freely flowing from the first fluid manifold 22 to the exit channel 28.

Fluid is selectively transferrable from the first fluid manifold 22 to the exit channel 28 across the first valve 32. In an embodiment, fluid is transferred from the first fluid manifold 22 to the exit channel 28 by applying a pressure differential to the exit port 30, thereby creating a negative pressure within the exit channel 28 which causes the fluid within the first fluid manifold 22 to cross or otherwise flow past the first valve 32 into the exit channel 28. The pressure differential can be created using a vacuum or pneumatic pressure, but for ease of explanation herein, the pressure differential will be referred to as the application of a vacuum. Once the fluid is within the exit channel 28, the fluid is isolated in the exit channel 28 and will not dilute or interfere with the fluid that has been previously distributed to the testing channels 26a, 26b, 26c, 26d.

In the illustrated exemplary embodiment of the testing module 16 shown in FIG. 2, a first distal end of each of four (4) testing channels 26a, 26b, 26c, 26d is fluidly connected to the first fluid manifold 22, wherein each of the testing channels 26a-d is spaced apart from the adjacent testing channel(s) 26a-d. It should be understood by one of ordinary skill in the art that although the exemplary embodiment shows four testing channels 26 fluidly connected to the first fluid manifold 22, the testing modules 16 can be formed to include any number of testing channels 26 fluidly connected to the first fluid manifold 22 for receiving a portion of the fluid to be tested by the testing channels 26. Each testing channel 26a-d is separated from the first fluid manifold 22 by a second valve 34 that is configured to selectively prevent fluid from flowing between the first fluid manifold 22 and the testing channel 26. In an embodiment, each of the second valves 34 is of the same type as the first valve 32, discussed above. In another embodiment, at least one of the second valves 34 is of the same type as the first valve 32. In a further embodiment, the second valves 34 are formed as different types of than the first valve 32. The second valves 34 can be mechanical valves, membranes, inserts or films positioned within the passageway, or formed from surface treatment of the passageway between the first fluid manifold 22 and the testing channels 26a-d. Each second valve 34 can be manually or electrically actuated or can be actuated due to a pressure differential thereacross. Exemplary embodiments of a second valve 34 may be a burst valve, a passive valve generated by hydrophobic surface treatment utilizing plasma etching, a hydrophobic porous membrane, a mechanical valve, or any other type of valve sufficient to provide selective fluid flow between the first fluid manifold 22 and each of the testing channels 26a-d.

In the exemplary embodiment illustrated, each testing channel 26a-d is formed of a metering portion 36, an analyzing portion 38, and a mixing portion 40 fluidly connected together, as shown in FIG. 2. Each of the portions is optionally separated by the adjacent portion therefrom by a valve or otherwise a hydrophobic barrier that allows selective movement of fluid between adjacent portions of the testing channel 26 across the hydrophobic barrier or valve. The metering portion 36 is positioned adjacent to the first fluid manifold 22, wherein the second valve 34 is positioned at one end of the metering portion 36. The metering portion 36 is located between the first fluid manifold 22 and the analyzing portion 38 of the testing channel 26. The metering portion 36 is a tubular passageway which allows fluid to readily flow therewith without appreciable bubble formation within the fluid.

A third valve 42 is positioned adjacent the opposing end of the metering portion 36, wherein the third valve 42 is located between the metering portion 36 and the analyzing portion 38 of the testing channel 26, as shown in FIG. 2. The third valve 42 is configured to selectively prevent free flow of fluid between the metering portion 36 and the analyzing portion 38. The third valves 42 can be mechanical valves, membranes, inserts or films positioned within the passageway, or formed from surface treatment of the passageway between the metering portion 36 and the analyzing portion 38. The third valves 42 can be manually or electrically actuated or can be actuated due to a pressure differential thereacross. Exemplary embodiments of any of the third valves 42 may be a burst valve, a passive valve generated by hydrophobic surface treatment utilizing plasma etching, a mechanical valve, or the like.

In an embodiment, a first pressure port 44 is positioned adjacent to the third valve 42 and is in fluid communication with a corresponding testing channels 26a-d of the testing module 16, as shown in FIG. 2. The first pressure port 44 extends in a substantially perpendicular manner relative to the metering portion 36. The first pressure port 44 is configured to allow a vacuum or pressure differential to be created within the testing channel 26 to aid in moving or pulling the fluid across the hydrophobic surfaces or hydrophobic porous membrane separating the portions of the testing module 16. A hydrophobic porous membrane (not shown) or other valve is positioned within the first pressure port 44 to prevent fluid from being withdrawn from the metering portion 36 through the first pressure port 44. As shown in FIG. 2, the first pressure ports 44 of each testing channel 26 for each testing module 16 is fluidly and operatively connected to a second manifold 46 (FIG. 1), which allows each of the first pressure port 44 of each testing module 16 within the cartridge 10 to be operated simultaneously. By creating a vacuum or pressure differential through each first pressure port 44, the pressure within the immediately adjacent portions of the testing channel 26 is reduced, thereby pulling the fluid toward the first pressure port 44. For example, once the fluid has been injected into the reservoir 20 and subsequently fills the first fluid manifold 22, creating a vacuum or pressure differential at the first pressure ports 44 pulls the fluid across the second valve 34 and into the metering portion 36. The vacuum or pressure differential creates enough of a pressure differential to pull the fluid into the metering portion 36 without further pulling the fluid through the first pressure port 44.

The second and third valves 34, 42 of each metering portion 36 are spaced apart a pre-determined distance to accurately retain a specific volume of fluid therebetween. By applying a vacuum or pressure differential to the first pressure port 44, a precise volume of fluid, or aliquot, is pulled into the metering portion 36 of each testing channel 26. The remaining volume of fluid that subsequently remains in the first fluid manifold 22 is withdrawn through the exit port 30, as explained above. Once the aliquot of fluid has been measured and retained within the metering portion 36 between the second and third valves 34, 42, the second and third valves 34, 42 can maintain the fluid therebetween without the vacuum or pressure differential being applied at the first pressure port 44.

The analyzing portion 38 of the testing channel 26 is positioned adjacent to the third valve 42 and the end of the metering portion 36, as shown in FIG. 2. The analyzing portion 38 includes an optical chamber 48 that is positioned between the third valve 42 and an optional fourth valve 50. The optical chamber 48 is configured to allow the fluid to be analyzed and monitored optically using spectrophotometry when at least a portion of the fluid is positioned within the optical chamber 48. The optical chamber 48 is configured to allow for accurate optical density measurement and can also be used as an immobilization or mixing chamber for the fluid. The optical chamber 48 provides the ability to monitor optical density of the fluid at all phases of analysis including: (1) before addition of or mixing with reagent(s) so as to get material and reader baseline data; (2) after addition or mixing of reagent/reactant but before reagent solvation to get fluid baseline data; and (3) continuous monitoring of the fluid during analysis and testing process. After the addition or mixing of reagent/reactant but before reagent solvation, the optical chamber 48 can be used to analyze for fluid present therewithin due to changes in optical reflection from surfaces of the optical chamber 48. This can be done to provide a starting point to improve accuracy of timing of subsequent optical measurements. The optical chamber 48 can be used to verify or check for correct amount of reagent by using natural absorption at normal optical monitoring wavelengths, use a tracer at normal optical monitoring wavelengths, use natural absorption at alternate optical monitoring wavelengths, and/or use a tracer at alternate optical monitoring wavelengths. A tracer is an inert compound that is added to a fluid to aid in determining the volume, fluid location and movement (fluid motions). The tracer may also be used to aid in validating the measurement data. Suitable tracers include, but are not limited to, dyes. Continuous monitoring of the fluid within the optical chamber 48 can be done on a much more frequent basis than standard multi-use plate readers to provide improved time resolution, better noise rejection, more able to accurately extrapolate to an endpoint for the data. Continuous monitoring of the fluid within the optical chamber 48 can also be done with fixed optics in a dedicated reader.

One or more portions of the cartridge may have modified surfaces. The portions with modified surfaces may include, but are not limited to, channels, reservoirs, and optical chambers. The surfaces may be modified by any means known to those of ordinary skill in the art, including but not limited to, applying a coating, radiation, plasma etching, or dissolved reagents which may dynamically cover the surface, so that the interaction of the surfaces and reagents or samples mimic that of standard microplate analysis so that the manufacturer's specifications or compendia standards for analysis are met.

In one embodiment, the surfaces of the microfluidic channels may be modified to control the biochemical LAL and LAL-reactive substance interaction or to control the surface energy. Controlling the level of the surface chemical interaction with the reaction chemistries may improve the repeatability and accuracy of the biochemical performance. For example, materials suitable for manufacturing the cartridges may also biochemically inhibit or enhance the LAL or LAL-reactive substance reaction chemistry. This biochemical interaction between the material surface and the reaction chemistries may be controlled or reduced with the application of a coating or through a chemical modification of the surface. Additionally, the unmodified surface of cartridge may have an undesirable surface energy for the microfluidics present in the cartridge. The surface energy may also be modified to a desired value through chemical modification or the addition of a coating to make the surface energy more hydrophilic or more hydrophobic, or to achieve any other surface energy between these states. By optimizing the surface energy, the microfluidics present in the cartridge may also be optimized.

Another means to modify cartridge surfaces include plasma etching, where the surface is modified by having it exposed to plasma to affect a particular final surface chemical structure. Different elements may be added to the plasma to modify the chemistry of the surface, for example, oxygen or ammonia. Additional means include the use of permanent static or dynamic surface coatings. Static surface coatings may be added to form a layer on the cartridge surface to change the surface character. Static surface coatings may be applied as a solution with a solvent and dried or applied by surface grafting wherein the coating is chemically bonded to the surface. Examples of static coatings that may be grafted or applied as a coating include, but are not limited to, polyethylene glycol (PEG) and collagen. Dynamic surface coatings may be added to the reagents, samples, or standards and coat the surface in situ as fluids move within the cartridge. When the coating materials are added to standards stored within the cartridge they can also be stored without these standards in testing channels that do not require standards. Examples of dynamic coatings include, but are not limited to PEG and surfactants like sodium deoxycholate.

In an embodiment, the optical reader (not shown) includes fixed optical components. The fixed optical components may include low cost LEDs and photodiodes. The reader can include band-pass filters to increase the accuracy of optical measurements. The reader can also be modulated or electronically chopped to provide a reduction in optical noise, reject ambient light, and reject stray light. The reader may also include multiplexed optical components such that the matrix of monitoring points can have a single component for each row or column and use a time-multiplexed reading scheme to lower component cost. Optical components such as windows, dark fields, apertures, lenses, reflectors, or diffusers can also be incorporated into the microfluidics cartridge itself to provide part of the optical path or increase the system's stability or sensitivity.

Suitable readers may use or perform a variety of optical sensing methods and measurements, including but not limited to, transmission, absorption, optical density, color, color value, hue, spectrum, turbidity, scattered light, chemiluminescence, and fluorescence.

The light sensed can be of a single wavelength, or spectral band, or multiple wavelengths or bands. Multiple light bands can be used to increase signal or reduce interference and noise. For example, monitoring at multiple frequencies for a change in optical density could reduce the interference of unstable sample color.

The sensing method used may be capable of sensing changes in the fluid remotely, including more complex optical methods such as Raman spectroscopy, magnetic resonance, and surface plasmon resonance, and non-optical methods such as electrical capacitance, viscosity, magnetism, sonic resistance, and sonic refraction.

A fourth valve 50 is an optional valve positioned between the analyzing portion 38 and the mixing portion 40 of each testing channel 26, as shown in FIG. 2. Similar to the first, second, and third valves 32, 34, 42, the fourth valve 50 is configured to provide a selective barrier between two adjacent portions of the testing channel 26, whereby the fluid is selectively prevented from flowing over or through the fourth valve 50. The fourth valve 50 is configured to selectively prevent the flow of fluid between the analyzing portion 38 and the mixing portion 40. The fourth valves 50 can be mechanical valves, membranes, inserts or films positioned within the passageway, or formed from surface treatment of the passageway between the analyzing portion 38 and the mixing portion 40. The fourth valves 50 can be manually or electrically actuated or can be actuated due to a pressure differential thereacross. Exemplary embodiments of any of the fourth valves 50 may be a burst valve, a passive valve generated by hydrophobic surface treatment utilizing plasma etching, a mechanical valve, or the like.

As shown in FIG. 2, the fourth valve 50 is positioned at one distal end of each mixing portion 40 and a second pressure port 52 is positioned at the opposing distal end of the mixing portion 40. The second pressure port 52 is in fluid communication with a corresponding testing channels 26*a*-*d* of the testing module 16. The second pressure port 52 extends in a substantially perpendicular manner relative to the mixing portion 40. The second pressure port 52 is configured to allow a vacuum or pressure differential to be created within the testing channel 26 to aid in moving or pulling the fluid across the hydrophobic surfaces or valves separating the portions of the testing module 16. A hydrophobic porous membrane (not shown) or other valve is positioned within the second pressure port 52 to prevent fluid from being withdrawn from the mixing portion 40 through the second pressure port 52. As shown in FIG. 2, the second pressure port 52 of each testing channel 26 for each testing module 16 is fluidly and operatively connected to a third manifold 46 (FIG. 1), which allows each of the second pressure port 52 of each testing module 16 within the cartridge 10 to be operated simultaneously. By creating a vacuum or pressure differential through each second pressure port 52, the pressure within the immediately adjacent portions of the testing channel 26 is reduced, thereby pulling the fluid toward the second pressure port 52. For example, once the fluid has been transferred into the metering portion 36, creating a vacuum or pressure differential at the second pressure port 52 pulls the fluid across the third and fourth valves 42, 50 and into the mixing portion 40. The vacuum or pressure differential creates enough of a pressure differential to pull the fluid into the mixing portion 40 without further pulling the fluid through the second pressure port 52.

The mixing portion 40 is an elongated tubular structure that forms the end of the testing channel 26 opposite the first fluid manifold 22, as shown in FIG. 2. The mixing portion 40 of the testing channel 26 is configured to allow the fluid being tested to be mixed with reagents or other substances within the mixing portion 40. The reagents or other reactants to be mixed with the fluid sample can be pre-loaded into the mixing portion 40, or the reagents or other reactants can be introduced into the mixing portion 40 during a testing process. In an embodiment, the volume of the mixing portion 40 is greater than the volume of the metering portion 36 to allow the fluid to be properly mixed within the mixing portion 40. The mixing portion 40 is configured to allow the fluid to be alternately drawn toward the second pressure port 52 and toward the first pressure port 44, moving it back and forth along channel 26 that comprises mixing portion 40, thereby causing the fluid to be mixed with any reagents or reactants within it.

The surfaces of the reservoir 20, transfer channel 24, first fluid manifold 22, and the testing channels 26 are configured to allow the fluid to flow therewithin. These surfaces also allow for capillary movement of the fluid within each portion of the testing module 16, wherein the movement of the fluid is selectively inhibited by the first, second, third, and/or fourth valves 32, 34, 42, 50. The testing modules 16 are configured to move the fluid from one location or portion of the testing module 16 to another by way of creating pressure differentials that cause the fluid to cross the valves and other barriers between portions of the testing module 16.

Figure 3:
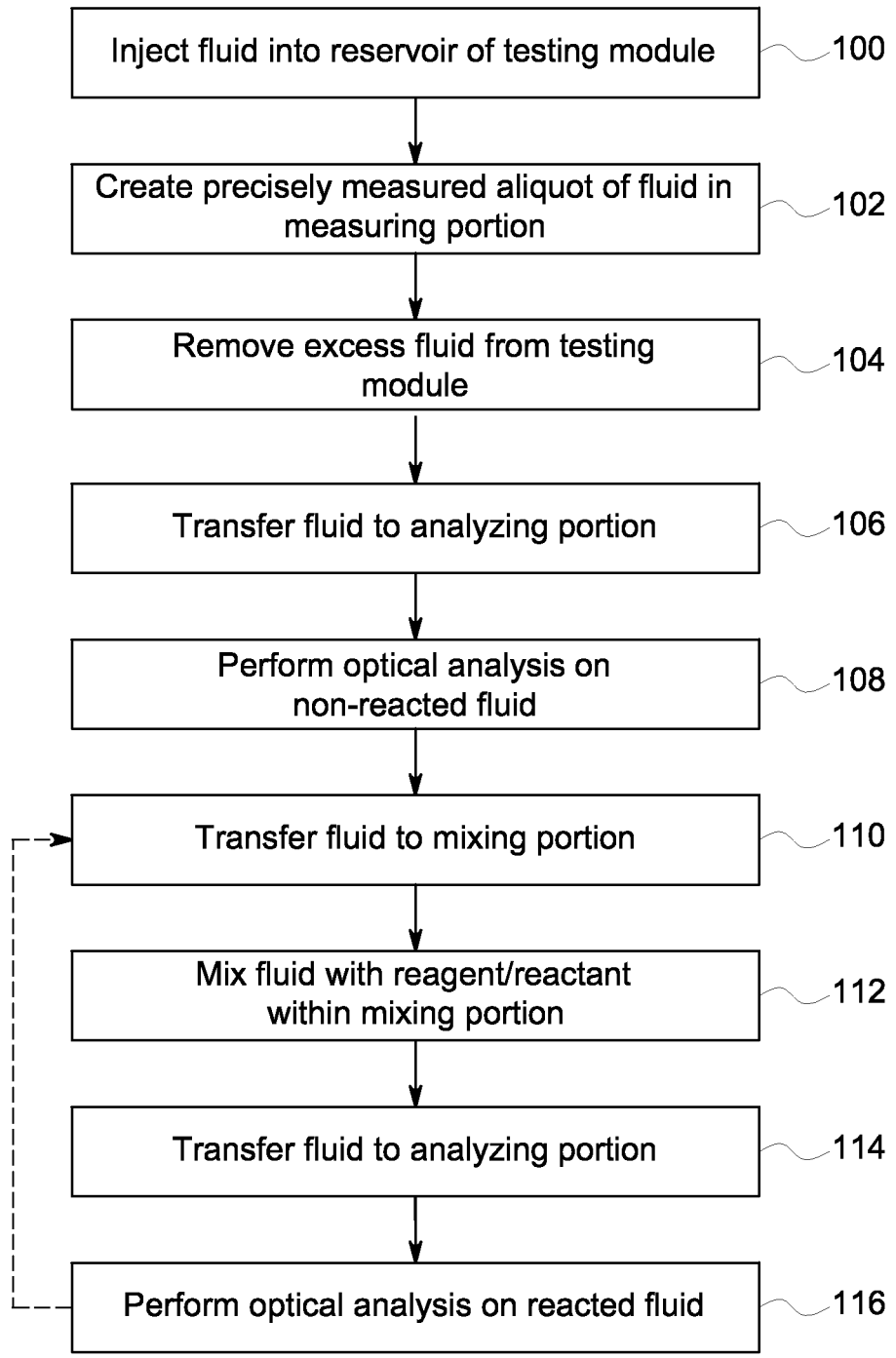
FIG. 3 is a schematic diagram of a testing process for a testing module in a cartridge.

An exemplary testing process or method within a testing module 16 of the cartridge 10 includes depositing a fluid into the reservoir 20 by way of the inlet port 18, as shown by the step 100 in FIG. 3. The fluid is then transferred from the reservoir 20 to the first fluid manifold 22 by way of the transfer channel 24. The next step 102 includes creating a precisely measured aliquot of fluid within the metering portion 36. This can be done by creating a pressure differential within the testing channel 26 by applying a vacuum to each of the first pressure ports 44 by way of the second fluid manifold 46 (FIG. 1), wherein this vacuum causes the pressure within the metering portion 36 (downstream side of fluid) to be less than the pressure within the reservoir 20 (upstream side of fluid). The pressure differential within the metering portion 36 causes the fluid to flow across the second valves 34 and into each metering portion 36. The vacuum can be created at all of the first pressure ports 44 of the testing module 16 simultaneously. In another embodiment, the vacuum is created sequentially or non-simultaneously to draw the fluid into the metering portions 36. The vacuum is applied to each first pressure port 44 until each of the metering portions 36 are completely filled, wherein a precise amount of fluid is contained between the second and third valves 34, 42. Once the aliquot of fluid is positioned within the metering portions 36, the vacuum at the first pressure ports 44 is ceased.

After an aliquot of fluid is contained in each of the metering portions 36 of the testing channels 26, the excess fluid that remains within the first fluid manifold 22, transfer channel 24, and reservoir 20 is transferred into the exit channel 28, as indicated in the subsequent step 104 in FIG. 3. The fluid is withdrawn by applying a vacuum to the exit port 30 which causes the pressure within the exit channel 28 (downstream side of fluid) to be less than the pressure within the first fluid manifold 22 (upstream side of fluid). The pressure differential within the exit channel causes the fluid to flow across the first valve 32 and into the exit channel 28 stopping at exit port 30. The fluid is isolated in the exit channel 28 and will not dilute or interfere with the fluid that has previously been distributed to the testing channels 26*a*, 26*b*, 26*c*, 26*d*. Once all of the excess fluid is stored in the exit channel 28, the vacuum applied to the exit port 30 can be ceased, but exit port 30 should be closed to venting so as to prevent the fluid stored within exit channel 28 to not be drawn back into first fluid manifold 22.

After the aliquots of fluid reside in each of the metering portions 36, the testing process for a testing module 16 next includes transferring the aliquot of fluid from each metering portion 36 into the analyzing portion 38, or into the analyzing portion 38 and the mixing portion 40 (when there is no fourth valve 50), as indicated by the step 106 in FIG. 3. Once at least a portion of the fluid is within the analyzing portion 38, the fluid is analyzed using photospectrometry or any other optical measuring process prior to the fluid contacting any reagent or reactant within the mixing portion 40, as indicated by the next step 108 in FIG. 3. The fluid is pulled into the analyzing portion 38, or into the optical chamber 48 and the mixing portion 40, of each testing channel 26 by creating a pressure differential within the mixing portion 40 by applying a vacuum to each of the second pressure ports 52 by way of the third fluid manifold 54 (FIG. 1), wherein this vacuum causes the pressure within the mixing portion 40 (downstream side of fluid) to be less than the pressure within the first fluid channel 22 (upstream side of fluid). The pressure differential within the mixing portion 40 causes the aliquot of fluid to flow across the third valves 42 and into each analyzing portion 38. The vacuum can be created at all of the second pressure ports 52 of the testing module 16 simultaneously. In another embodiment, the vacuum is created sequentially or non-simultaneously to draw the fluid into the analyzing portion 38. The vacuum is applied to each second pressure port 52 until the entire aliquot of fluid flows across the third valve 42 and a measurable amount of the fluid is contained in the analyzing portion 38. Once the entire aliquot of fluid is located within the analyzing portion 38, or into the optical chamber 48 and the mixing portion 40, the vacuum at the second pressure ports 52 is ceased and the non-reacted fluid is analyzed in the optical chamber 48.

For the testing process for a testing module 16 in which the testing channels 26 include a fourth valve 50 positioned between the analyzing portion 38 and the mixing portion 40, the vacuum is applied to the second pressure ports 52 until the entire aliquot of fluid is transferred into each of the optical chambers 48 and contained between the third and fourth valves 42, 50, as indicated by the step 106 in FIG. 3. Once the entire aliquot of fluid is positioned within the analyzing portion 38 of each testing channel 26, the vacuum at the second pressure port 52 is ceased, allowing the non-reacted fluid within the optical chamber 48 to be analyzed, as shown by the step 108 in FIG. 3. Once the fluid has been analyzed, the entire aliquot of fluid is transferred to the mixing portion 40 by applying a vacuum to the second pressure port 52 to create a pressure differential across the fluid to draw the fluid across the fourth valve 50, as shown by the step 110. After the aliquot of fluid is transferred to the mixing portion 40, the vacuum at the second pressure port 52 is ceased.

Once the aliquot of fluid is located within the mixing portion 40 of each testing channel 26, or within the analyzing portion 38 and the mixing portion 40, the fluid is mixed with the reagent/reactant(s) within the mixing portion 40, as shown by the step 112 in FIG. 3. In an embodiment, the reagent/reactant within the mixing portion 40 are pre-loaded or pre-deposited within the mixing portion 40 such that the reagent/reactant is located within the mixing portion 40 prior to the beginning of the testing process for a testing module 16.

In another embodiment, the reagent/reactant within the mixing portion 40 is introduced into the mixing portion 40 after the beginning of the testing process for a testing module 16. Mixing fluid with the reagent/reactant within the mixing portion 40 involves alternatingly applying a vacuum to the first and second pressure ports 44, 52 while ensuring no vacuum is being applied to the opposing pressure port, thereby causing the fluid to move toward each respective pressure port to cause movement of the fluid within the mixing portion 40 to allow the fluid and reagent/reactant to mix. In an embodiment, a continuous vacuum is applied, wherein the vacuum is applied to either the first or second pressure port 44, 52 while the opposing pressure port has no vacuum applied thereto, and the vacuum alternates between the first and second pressure ports 44, 52. In another embodiment, a vacuum is applied to one of the first or second pressure ports 44, 52 to cause the fluid to move theretoward and then the vacuum is ceased for a pre-determined amount of time before applying a vacuum to the other of the first or second pressure port 44, 52 to cause the fluid to move in the opposite direction within the mixing channel 40. It should be understood by one of ordinary skill in the art that there may also be a pre-determined dwell time in which no vacuum is applied to either the first or second pressure port 44, 52. The number of times that the vacuum is applied to each of the first and second pressure ports 44, 52 can vary depending on the particular type of testing or reagent/reactant within the mixing portion 40, but it should be understood by one of skill in the art that the fluid can be moved toward each of the pressure ports any number of times to sufficiently mix the fluid and the reagent/reactant.

The microfluidic properties of the cartridge 10 provides for slug flow (bolus mixing) of the fluid therewithin. The microfluidics involves flow in and out of chambers and channels where the flow path changes depending on direction.

In another embodiment, once the aliquot of fluid is thoroughly mixed with the reagent/reactant in the mixing chamber 40, the entire aliquot of fluid is transferred to the analyzing portion 38 to continue reacting with the reagent/reactant and the mixed fluid is analyzed and monitored over a period of time within the optical chamber 48.

The subsequent step in the testing process for a testing module 16 includes transferring the reacted fluid to the analyzing portion 38 of each testing channel 26, as shown by the step 114 in FIG. 3. This transferring step is accomplished by applying a vacuum to the first pressure port 44 while the vacuum at the second pressure port 52 is ceased to cause at least a measurable portion of the fluid to move or flow into the optical chamber 48 of the analyzing portion 38. Once at least a measurable amount reacted fluid is transferred to the optical chamber 48, the next step includes performing an optical analysis of the reacted fluid, as shown by step 116 in FIG. 3. In an embodiment, this optical analysis of each reacted fluid within the testing module 16 is the end of the testing process for a testing module 16. In another embodiment, after the first optical analysis is completed, the reacted fluid can be transferred into the mixing portion 40 for further mixing or to allow the reacted fluid additional time for further reacting, wherein the reacted fluid can be returned to the optical chamber 48 for subsequent optical analysis. These steps can be repeated, if necessary, to obtain additional data for the reacted fluid over time.

FIG. 4A illustrates an exemplary summary of a testing process for a testing module. The pressures are shown in centimeters of hydrostatic head, wherein negative pressure indicates a vacuum, and the valve pressures are shown as positive pressures. The first valves 34 are formed of a swelling polymer valve or restriction to allow a vacuum from the first pressure ports 42 during steps 5, 6, and 7.

FIG. 4B illustrates another exemplary summary of a testing process for a testing module. The pressures are shown in centimeters of hydrostatic head, wherein negative pressure indicates a vacuum, and the valve pressures are shown as positive pressures. The first valves 34 are formed of a swelling polymer valve or restriction to allow a vacuum from the first pressure ports 42 during step 5.

Figures 5C, 6:
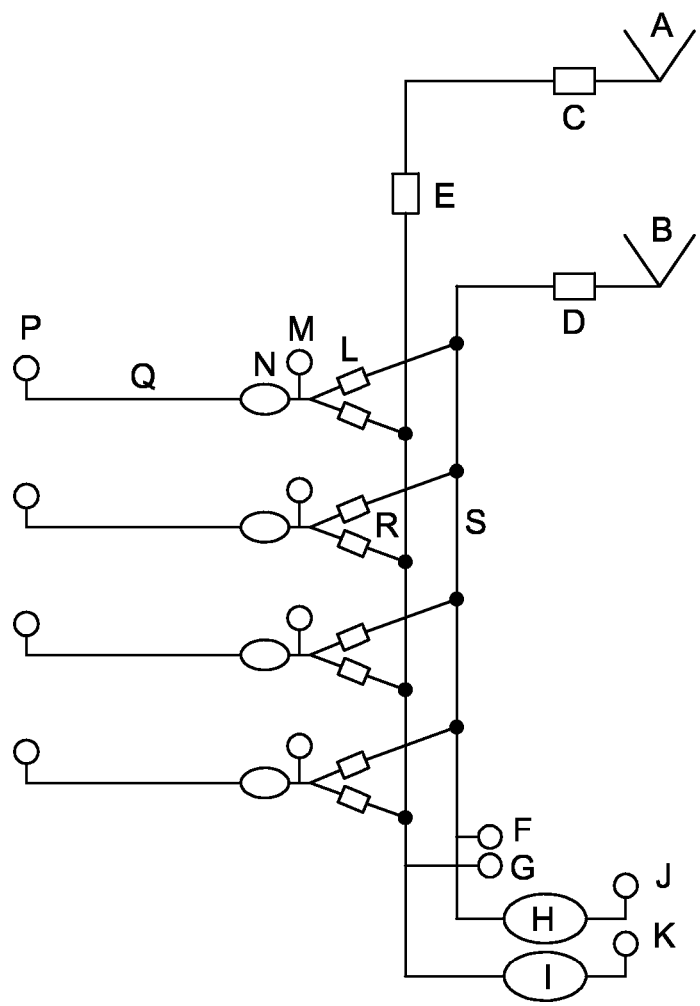
FIG. 5C is a chart of ranges for reagents used in a cartridge.
FIG. 6 is another exemplary embodiment of a testing module.

As explained above, an exemplary embodiment of a cartridge 10 includes twenty-four (24) testing modules 16 formed therein, wherein each testing module 16 is configured to test a separate fluid. FIG. 5A illustrates the reagent/reactant within each mixing portion 40 of a cartridge 10 having twenty-four (24) testing modules, wherein each testing module 16 includes four (4) testing channels 26. FIG. 5B illustrates another embodiment of the reagent/reactant within each mixing portion 40 of a cartridge 10 having twenty-four (24) testing modules, wherein each testing module 16 includes four (4) testing channels 26. The table of FIG. 5B indicates that as shown in FIG. 5C, the lowest, mid-range, and highest endotoxin levels depend on the range of the particular cartridge 10, wherein the range level within a single cartridge 10 is the same for each testing module 16. The units of the different ranges in FIG. 5C are in EU/mL (Endotoxin Units per milliliter). Calibration replicates are averaged to generate a calibration curve. A negative control must be statistically different than the lowest calibration level. Sample analysis replicates are averaged for each reported value. Positive control spikes are averaged and the difference between spiked analysis and base analysis must be within 50% and 200% of the mid-range value for a valid analysis. The calibration analyses for each exemplary cartridge 10 shown in FIGS. 5A-5B are based upon a triple replicate control. The dots in the tables shown in FIGS. 5A-5B indicate the existence of interim values. The interim values may be readily determined by those of ordinary skill in the art.

In another embodiment, where non-compendia methods are acceptable or have been validated as being equivalent and acceptable to regulatory agencies, a stored calibration based on historical measurement data can be used instead of the results from individual standards.

FIG. 6 illustrates another exemplary embodiment of a cartridge 10 and the components thereof. In operation, the first step includes adding liquid LAL added to A as well as adding a fluid sample to B, wherein the volume is in slight excess of what is needed to perform the testing process for a testing module. Next, a vacuum is applied at F and G to fill distribution channels R and S. A vacuum at less pressure than will overcome burst valves L is then applied at M, thereby filling the branches leading to each optical channel N with a metered aliquot of sample or LAL. Next, a vacuum is applied at J and K with F and G not vented to fill H and I with excess reagent and LAL, clearing R and S. A vacuum is then applied to P with F vented (and G not vented) which will pull the fluid sample into mixing channel Q. Alternating application of the vacuum between M and P shuttles the fluid sample back and forth within Q to cause mixing with the LAL-reactive substances (if present). Next, applying a vacuum at M moves the fluid sample into the optical chamber. Once the fluid sample is in the optical chamber, the next step includes closing the vent to F and venting G, wherein a vacuum is applied to P to pull over the fluid sample followed by the LAL reagent. The subsequent step includes alternating a vacuum at M and P to shuttle these two fluids back and forth within Q, mixing them together. A vacuum is then applied at M to move the sample into optical cell N, where the reaction is monitored.

The form and shape of the cartridge is not limited to the geometries above. The cartridge may also be in a chip or disc shape. Alternate suitable geometries may also occur to persons of ordinary skill in the art and are within the scope of this invention.

Figure 7:
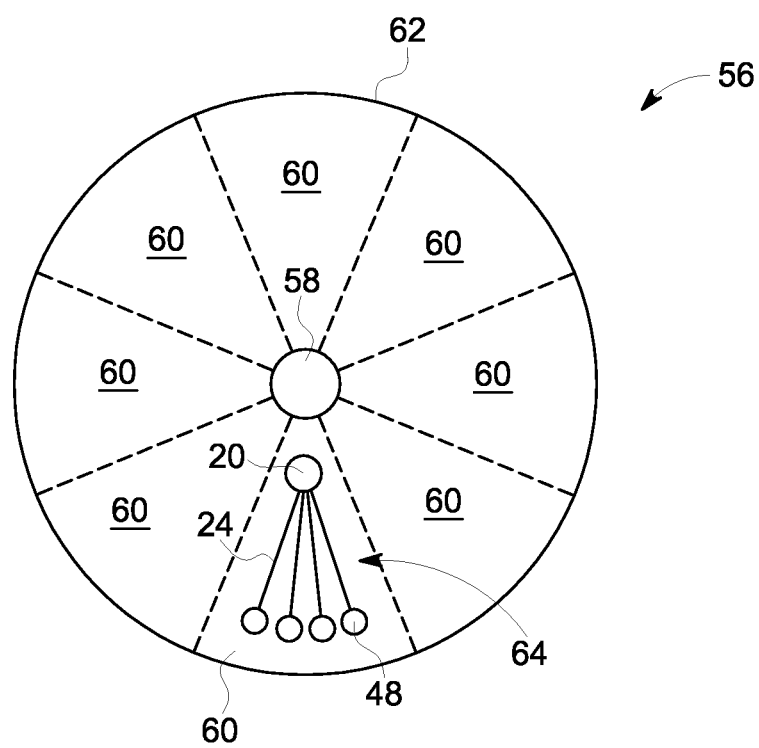
FIG. 7 is an exemplary embodiment of a microfluidic disc.

FIG. 7 illustrates another exemplary embodiment of a cartridge 10, wherein the cartridge is in the form of a microfluidic disc. The microfluidic disc may have all the components and elements of cartridge 10 described above, including but not limited to, a plurality of testing modules, inlet ports, testing channels, metering portions, analyzing portions, mixing portions, valves, etc. FIG. 7 shows a layout of an embodiment of microfluidic disc 56 having a hole for a hub 58 in the center of disc 56 for removably mounting to a spindle of a reader (not shown) for spinning the disc.

The spindle may be connected to a motor (not shown) thereby allowing disc 56 to be spun by the motor. It is anticipated that the motor can be any type of mechanical actuator that is capable of rotating the disc 56. The disc may be rotated at a speed sufficient to apply centrifugal forces to the fluid samples therein and motivate aliquots within the testing channels to move across the valves. Through rotation at varying speeds such a system could also perform all the necessary fluid motions for the entire network through changes in force, fluid pressure, or pneumatic pressure created by previous fluid motions.

Individual samples, portions of samples, references or controls, or portions of references or controls, may be analyzed by groups of optical chambers 48 segregated into testing areas 60. In typical embodiments of disc 56, radial testing areas 60 are laid out in a radial pattern. However, it is anticipated that a person having ordinary skill in the art can choose another pattern.

Each testing area 60 may comprise a fluidics network 64. Each fluidics network 64 may comprise a reservoir 20. Samples or references, reagents or standards may be placed in reservoirs 20, nearer the hub 58 of disc 56. When the disc 56 is spun, the fluid will move through open testing channels 26 towards the outer edge 62 of disc 56. In some embodiments, testing channels 26 may also include a metering portion 36 and mixing portion 40 to aliquot and mix the samples as they move towards the optical chambers 48. As described above, the mixing portion 40 may be pre-loaded with reagents, standards or other reactants.

In most embodiments of disc 56, the sample inserted into reservoirs 20 will typically be split into four aliquots, with each aliquot being delivered to a separate optical chamber 48. This is due to the fact that current compendia requirements are for each sample to be analyzed four times, twice without addition, and twice with a positive control added. This is also convenient for calibration and negative control analyses, because the "universal" implementation of these may require twelve (12) analyses using LAL Reagent Water as the sample, which can easily be accomplished by 3 sets of 4 analyses using the same layout, in which three reservoirs 20 would be provided with the sample, and the sample in each reservoir 20 would be split into four aliquots and provided to individual optical chambers 48, thereby creating the necessary twelve (12) analyses. It is contemplated that some embodiments of disc 56 may employ a 12-wide layout from a single, larger reservoir 20 in which a single reservoir 20 would be provided with the sample, and the sample would be split into twelve aliquots and provided to individual optical chambers 20, thereby creating the necessary twelve (12) analyses. It is envisioned that reservoir 20 in embodiments which provides samples to 12 analyses will be larger than reservoir 20 in embodiments that provides samples to four analyses.

In some embodiments of disc 56, valves control the flow of fluid in fluidics network 64. The valves described above may be implemented to perform such actions as to stop the flow of fluid temporarily or permanently, to regulate the flow of fluid through the disc, and to regulate the reaction process taking place in disc 56. One type of valve is a burst valve. A burst valve uses the channel surface energy and capillary force to control fluid flow. It is known that capillary action transports fluid by wicking or otherwise drawing the fluid up small channels. The surface tension of the fluid provides the motivating force because the fluid wants to wet the channel walls, thereby the fluid draws itself up the channel until the pressure in the channel equals the surface tension motivating force. The same surface tension force can also be used to keep fluids from flowing through channels by constructing the channel out of a hydrophobic material or coat the walls of the channel with a hydrophobic material, instead of a hydrophilic material. Hydrophobic materials repel water and hydrophilic materials attract water (are wetting). One exemplary hydrophobic material is a hydrophobic micro-porous membrane, which, due to the material pore size, allows air to pass through, but not water. The small size of the hydrophobic micro-porous membrane pores requires a large pressure, in the form of capillary pressure, to force water through the pores. This capillary pressure is dependent on the surface energy of the fluid in the channel, the surface energy of the channel material or interior channel coating, and the size and geometry of the channel. Disc 56 may be made of a variety of materials including, but not limited to, polystyrene, cyclic olefin copolymer, and glycol-modified polyethylene terephthalate. In some embodiments of disc 56, carbon may be added to make the polystyrene black to aid in optical absorbance methods.

Each cartridge 10 contains at least one sample fluid, which itself consists of at least two replicates of a standard analysis and two positive controls, i.e. spiked with LAL-reactive substances; and a calibration curve formed with at least 3 points and negative controls (blanks), each with at least 2 (or 3) replicates.

When spikes are made from dried standard, the volumes of the sample and reagent are identical to the other analysis and calibration tests. When the spike is liquid, it can be added as a "hot spike" which is an accepted method in the industry, recommended by manufacturers, and accepted by regulators. In this method, a solution of standard 10 times the desired spike concentration is added to a sample. The volume of standard added is 10% of the sample volume. The standard amount of LAL reagent is added, and the resulting mixture is monitored in a cell with a path-length 5% longer than a standard non-spiked cell's length. This mimics the hot-spiking method used in microplates, where the volume of combined samples and reagent, and thus the optical column and path length, is 5% greater with hot spiked samples.

In another embodiment, blank water may be used as a source of the sample for the blank analysis and to distribute and dilute a single standard at the highest level. Thus, the standard is diluted as necessary by distribution, precise metering, and mixing to produce the other standards or spikes. For example, blank water and the highest level of standard may be added to the cartridge. The added blank water may then be used as is for the blank analysis with 3 replicates. The added highest level of standard is also used as is for the highest level standard analysis with 3 replicates. The microfluidics network may then be used to meter amounts of blank water and the highest level standard and mix them together to form one or more intermediate level standards. The metering and mixing steps may be done separately for each replicate. Likewise, either the highest level standard or some of the intermediate level standard (which would need to be "left over" from the analyses that use it) and additional blank water may be used to make the lowest level standard. If standard levels are decreased by 90% at each step, then the first dilution would be to 1:9 (1 measure of standard to 9 measures of blank water). The lowest level could either be made from another 1:9 dilution of the intermediate level standard or a 1:99 dilution of the highest level standard.

Each cartridge 10 is filled with fluid samples prior to beginning a testing process for a cartridge. The fluids are input into the inlet ports 18, wherein the fluids can be input manually or automatically. Once the fluids are input into the respective inlet ports 18, the cartridge 10 in inserted into a reader (not shown) that is configured to be fluidly connected to the second and third fluid manifolds 46, 54 (FIG. 1) on the upper surface of the cartridge 10. After inserting the cartridge 10 into the reader, the testing process for a module, as explained above, is started. During the testing process for a module, when the fluid is positioned within the optical chamber 48 for optical analysis, the reader is configured to conduct optical testing, such as optical spectrometry, recording the data analyzed, and compile the recorded data.

The cartridge 10 provides faster analysis time compared to standard microplate methods for testing for LAL-reactive substances as well as any other fluid testing. The cartridge 10 requires much less preparation time than typical microplates, resulting in less chance of contamination, easier to integrate into other laboratory tasks, and lower costs. The microfluidic test cartridge 10 meets all the valid test requirements of USP <85> Bacterial Endotoxin Test for turbidimetric or chromogenic techniques, including preparatory testing which includes assurance of criteria for the calibration curve and test for interfering factors, which includes the test procedure, calculation, and interpretation (in the case of water for injection) is the result is less than 0.25 EU/ml and in the case of product the endotoxin is less than the limit for the product. There is no attachment of reagents into the measuring channel 36 connecting the inlet port 18 and the optical chamber 48 to allow the initial critical optical quality measurement of the fluid sample prior to the addition or mixing of reagents with the fluid. Additionally, each fluid sample, blank, and calibration LAL-reactive substance test may be internally validated.

The cartridge 10 may also include a means to validate the tests or analysis. "Validate" as used herein means to substantiate, confirm the quality of, or establish the certainty of the analysis or progress of the analysis. When validating the suitability of the analysis, compendia methods may be used wherein at least two positive controls (samples spiked with LAL-reactive substances at the middle of the calibration range), three negative controls (blanks), and any other parameters specified by the manufacturer or compendia. The positive product control spikes must meet compendia requirements (between 50% and 200% spike yield), the negative control (difference between lowest level and blank, with the blank having a lower response level), and the manufacturers specification (e.g. the difference between a 0.005 EU/mL sample and blank, or onset time limits for certain standards). If these analyses are successful, they validate that the system and reagents are operating to specification. To validate the data stream means that the data streams' behavior statistically corresponds to the expected behavior based on historical measurement data or the known reaction kinetics of the reaction between the detection reagent and LAL-reactive substance. This shows that the data stream is being generated by a change in the analysis chamber based on the LAL reaction and not a change in the chamber or optical path based on some abnormality, such as a bubble. Ultimately this differentiation would itself be validated by multiple tests on different reagents and lots and induced anomalies to confirm its operation, including, but not limited to, sample critical optical quality blank reading, mixed sample/reagents/optional LAL-reactive substances, initial optical reading, smoothness of the change and rate of change of the critical optical quality, closeness of fit to theoretical expected change, expectations on the noise level of the data, and the like. If test results appear incorrect the testing process for a module will be stopped and an error message will be sent without producing an LAL-reactive substances measurement result.

The cartridge 10 is configured to prevent introduction errors by the fluid sample. In an embodiment, the cartridge 10 includes visual feedback for placement of fluid samples, which may include colored or marked fields or other active optical feedback. The cartridge 10 is also configured to minimize pipetting errors. Each fluid sample is automatically aliquoted for multiple testing. Each fluid sample is injected in one reservoir 20 (in an embodiment about 100 µl of fluid) and split into 4 equal aliquots of fluid to meet the requirements of USP <85> Bacterial Endotoxin Test standard. In an embodiment, each aliquot volume measured in the metering portion 36 of the testing module 16 is about 10% less than the 25 μl (one-fourth of the volume of fluid introduced into reservoir) to minimize sample introduction errors by users. The user only injects fluid samples and LAL-reactive substance free water (blank water) into the cartridge 10. Because of the reduced amount of fluid sample used for testing, a similarly less amount of reagent is required for a testing process, and a reduced amount of necessary reagent results in a cheaper test for LAL-reactive substances.

The cartridge 10 is also configured to predict BET measurement results. The cartridge 10 includes means to accurately predict or forecast the concentration of endotoxin or other LAL-reactive substances in the samples by monitoring the critical optical quality (transmission, absorption, turbidity, chemiluminescence, or florescence) as a function of time and applying various prediction algorithms. The prediction is used to speed up measurement time to final results. The cartridge 10 also allows for signal extraction from noise during the optical analysis. The cartridge 10 also provides for the use of the kinetic reaction model or other reaction models. As used herein, "predict" or "forecast" means to assess the magnitude that a quantity will have at a specified time in the future. Forecasting may be achieved by any method known to those of ordinary skill in the art, including, but not limited to, any linear or non-linear method which processes the data in such a way that information is maintained suitable and predictions may be made as to the behavior of the data in future times. Forecasting methods include, but are not limited to, curve fitting and extrapolation.

The cartridge further includes optional active fluid sample degassing using hydrophobic membranes and multiple sample movement past the membrane. Optionally, degassing may be achieved while the sample is not moving and is in static contract with the membrane by reducing the pressure on one side to remove gas from the liquid or directly from bubbles. Other de-bubbling or gassing methods include a) eliminating bubbles by pressurizing a portion of the fluidics, all of the fluidics, or the entire fluidic structure so that gas does not transfer out of the liquid or b) eliminating bubbles by trapping them in a device created to prevent the bubbles from travelling, such as a membrane or matrix of restrictions. Active agents can also be used that reduce the formation of bubbles, such as surfactants and anti-foaming agents, and these can be immobilized in the cartridge or introduced by the user.

The cartridge 10 includes ways to indicate which inlet port is to be filled by the user with an option to associate an entered label or identifier for the sample into a data collection interface, automatic analysis of results including calculations, automatic report of all results required by the user to meet regulatory requirements. The cartridge reader or preparation device can also include means of restricting sample access to inlet ports to assure correct sample introduction. The cartridge 10 also allows for the interface to generate reports to include all relevant information on cartridge and reagent lot number, age and shelf life limits. For example information or markings the cartridge may be transferred either manually or automatically to the reader and recorded.

Hydrophobic membranes are used in the cartridge 10 to motivate the sample fluid aliquots with the application of appropriate pressure or vacuum on the external side of the membrane. This motivation means is used to precisely measure aliquots of the fluid samples, mix the reagents into the fluid sample through the movement of the fluid aliquots, and precisely position the aliquot in the optical chamber 48 for measurement and analysis. Hydrophobic patches or membranes can be used to assist in the positioning of the fluid aliquots within the cartridge and can be used to create burst valves to further improve positioning of sample fluid aliquots within the testing modules 16.

Reagents—including LAL, LAL-reactive substances, and optional chromogenic reagents, and the like—can be pre-loaded at the correct levels in the cartridge by any practical means including immobilization of the reagents on to the walls of the testing channels 26, addition of dissolvable reagents in various forms (pellets, powders, or beads), or attached to dissolvable and non-dissolvable films or forms inserted into the cartridge 10.

The cartridge 10 is configured to reduce or eliminate contamination. A means can be used to seal the inlet port, exit port, and first and second pressure ports to block the transmission of water, oxygen, environmental endotoxin and bacteria and other LAL-reactive substances. The cartridge 10 can also include a means to keep the dried reagents at a relative humidity less than 4% during cartridge manufacture and storage.

The optical reader (not shown) can include a heater or other apparatus to heat the cartridge to a controlled temperature, and, in an embodiment, prior to introduction of the fluid samples. The optical reader can be configured to measure the optical density of the samples before, during, and at the end of the reaction. Other embodiments of the cartridge 10 can be configured to measure critical optical qualities in standard commercially available microplate readers with the use of a second separate heater or heating apparatus to preheat, and motivate sample positioning to fluid aliquots, mix reagents with fluid samples and place fluid samples into the optical chambers 48. The cartridge 10 can then be placed into a standard microplate reader for reaction analysis and LAL-reactive substances measurement.

The cartridge 10, as explained above, can include reagents/reactants, such as, for example, LAL, LAL-reactive substances, and/or chromogenic reagents. The reagents/reactants are stabilized for long shelf life with addition of additives using slow or rapid drying methods. The reagents/reactants can be configured to control solvation rate when reconstituted with the fluid sample. Both slow drying and rapid lyophilization can be used, based on proven ability to re-dissolve without loss of sensitivity for the LAL-reactive substances measurement. Extraction of pyrogenic natural materials from bacteria can be used to create material that solubilizes quickly, prevents bio-molecular aggregates, and has good stability. The reagents/reactants are deposited in the testing modules 16 to control deposition accuracy, isolation of different reagent components to prevent premature interaction, and optimized mixing from best physical arrangement. The reagents are designed for fast solvation to increase accuracy of optical measurement. The rate of solvation should be controlled so that the mixing with the fluid sample has maximum efficiency. Solvation of the reagents can be controlled so that optical analyses can start at known or pre-determined times, which increasing accuracy of the optical measurement.

Bubbles can interfere with motion of the fluid and the optical properties of the fluid, and their control is important to a robust analytical system. Bubbles within the fluid samples can be avoided by: (1) drying the reagent/reactant so that bubbles are not generated during solvation with the fluid; (2) fluid channels are designed to avoid generating bubbles; (3) fluid motion is designed to avoid generating bubbles; (4) surfaces of the testing channels 26 are formed so that bubble nuclei are not made; (5) cartridge 10 is assembled so that bubble nuclei are not made; and (6) reagents are immobilized so that bubble nuclei are not made. Moreover, should any bubbles remain in the samples, the bubbles will show up as an anomaly in the validation process and the analyses may be rejected.

The membrane-based microfluidic cartridge 10 utilizes a vacuum or pressure to motivate fluid movement within the channels and portions thereof. Alternatively, the fluid may be motivated by spinning the cartridge. In an embodiment, the cartridge 10 utilizes a combination of hydrophobic microporous membrane(s) and channel geometry to accurately control aliquoting of the fluid sample. In another embodiment, the cartridge 10 utilizes a combination of hydrophobic microporous membrane(s) and surface energy to accurately control aliquoting of the fluid sample. In a further embodiment, the cartridge 10 utilizes a combination of hydrophobic microporous membrane(s) and geometry to accurately position the fluid sample, particularly for optical measurement. In yet another embodiment, the cartridge 10 utilizes a combination of hydrophobic microporous membrane and surface energy to accurately position the fluid sample. The cartridge 10 can utilize partial vacuums generated by secondary flow through membranes. In another embodiment, the cartridge 10 is a microfluidic system where the fluid is motivated and controlled by capillary forces.

In another embodiment a volumetric pump, such as a syringe pump, is attached to the testing module 16 at the four pressure ports 52 shown in FIG. 2. The volumetric pump is used to aliquot the liquid sample contained in reservoir 20, first fluid manifold 22, and transfer channel 24 by moving the respective four aliquots to a position at third valve 42. At that point in time all the excess sample in reservoir 20, first fluid manifold 22, and transfer channel 24 is moved into exit channel 28 or is removed or drawn from the system as waste, leaving only air in first fluid manifold 22. The volumetric pump then applies a vacuum to pressure port 52 to move the sample into the optical chamber 48 for an optional initial blank optical measurement. The initial blank measurement may be used to determine whether the sample has completely filled optical chamber 48 or whether there is a bubble in the system. This is possible because the optical signal is very different when there is a bubble in the optical chamber 48 and when there is only water sample completely filling the optical chamber 48. Then the sample is moved into mixing portion 40, where optional reagents and optional LAL-reactive substances have been placed. The volumetric pump is then used to reverse the direction of movement and to move the sample from mixing portion 40 back into optical chamber 48 to completely fill it. Optionally the sample is farther moved into metering portion 36 until the optical property of optical chamber 48 shows the presence of a bubble and the flow is stopped. The combined sample and reagent materials are moved back towards second pressure port 52, completing one mixing cycle. This process can be repeated multiple times until the mixing is complete. The number of back and forth moves required to mix the reagents and sample water can be fixed determined by prior experiments. Alternatively the mixing process can be monitored and stopped when the optical property of the mixed sample and reagent stops changing. This is measured by detecting the changes in the optical response from the mixed sample and the reagents during each mixing cycle. It should be noted that the optical property is measured only when the optical chamber is completely full and no bubbles are present.

In another embodiment, an optional hydrophobic membrane may be used for valve 42. A vacuum may be applied on the non-liquid side of the membrane. The vacuum may be used to degas the sample and reagent mixture as the mixture moves back and forth through measuring portion 40. Once the sample and the reagents are mixed they are moved to optical chamber 48 and the optical or other property is measured as a function of time to determine the amount of LAL-reactive substances present at the chosen reaction temperature. This embodiment is simpler as described in prior embodiments, as it may be used without valves 32, 34, and 42. The fluid positioning is accomplished by precise control of the volumetric movement of the pump or by optical feedback from the optical sensor measuring the liquid or lack of liquid in optical chamber 48. This embodiment can have a separate volumetric pump associated with each pressure port 52 or one pump can be connected to multiple pressure ports 52 through manifold 54. Additionally this embodiment may be used in an online LAL-reactive substances detection mode where each fluidic section 34, 36, 40, and 48 can be separately sealed off from the environment at location 34. The seal can be broken when a port is attached to it that contains a fresh sample collected online from a water system. The number of fluidic sections 34, 36, 40, and 48 can vary from one to four or more. In this way a cartridge with many such fluidic sections is manufactured and loaded into a sample collection device with a port that delivers the fresh sample to the respective sealed port 34 on each fluidic section. The cartridge or the sample collection device can move to each new connection to the sealed port 34. This approach can be operated in a fashion to meet the regulatory requirements or in a fashion suitable only for process control that does not have all the measurement and validation elements of a regulatory method.

In a further aspect of the inventions, a single sample is split into separate portions, distributed to individual microfluidic netoworks, and aliquoted for each individual test. In all cases the sample volume does not need to be precise, but simply enough to cover all aliquots and not so much that it overflows the apparatus.

Also, sections can be arranged on a single or multiple cartridges such that the sections are normally stored in an environment where the reagents have long-term stability, such as a low temperature, and a section or group of sections can be moved out of this storage area and into an area where conditions are regulated for analysis, such as being heated to 37° C., to perform actual assays.

In one aspect of the present invention, a microfluidic cartridge for testing fluid samples is provided. The cartridge includes at least two testing modules, wherein each testing module includes an inlet port for receiving one of the fluid samples, and at least four testing channels in fluid communication with the inlet port. Each of the testing channels may include a metering portion for metering an aliquot of the fluid sample, an analyzing portion, and a mixing portion. A valve may be positioned between the metering portion and the analyzing portion to selectively fluidly separate the metering portion from the analyzing portion. Each testing module may have at least one testing channel with at least one reagent isolated therein.

In another embodiment, at least one testing module is a calibration module comprising at least eight (8) testing channels. At least two channels may have no LAL-reactive substance therein, at least 2 channels may have a first amount of a LAL reactive substance isolated therein, at least 2 channels may have a second amount of a LAL reactive substance isolated therein, and at least 2 channels may have a third amount of a LAL reactive substance isolated therein. In another embodiment, the first, second, third amounts may be the same or different. If endotoxin is used, the first amount may be chosen such that when the endotoxin is in a solution, the concentration ranges from 0.005 to 0.5 EU/mL. Similarly, the second amount may range from 0.05 to 5.0 EU/mL and the third amount may range from 0.5 to 50 EU/mL.

In yet another embodiment, at least one testing module is a sample measurement module comprising at least four (4) testing channels. At least two channels may have no LAL-reactive substance therein, and at least two channels may have a spike with a fourth amount of a LAL-reactive substance isolated therein. If endotoxin is used, the fourth amount may be chosen such that when the endotoxin is in solution, the "spikes" have the characteristics described earlier in the specification.

In another embodiment, all of the testing channels may have at least one additional reagent isolated therein. The additional reagent may comprise a detection reagent. In another embodiment, the microfluidic cartridge may further comprise an exit port in fluid communication with the inlet port for removing excess of the fluid sample.

In yet another embodiment, the valve is configured to allow vacuum, centrifugal forces, or pneumatic pressure to motivate the aliquot across the valve to flow from the metering portion to the analyzing portion. In another embodiment, the microfluidic cartridge may further comprise a first pressure port positioned within the metering portion and adjacent to the end of the analyzing portion for creating a pressure differential within the testing channel. In yet another embodiment, the microfluidic cartridge may further comprise a second pressure valve positioned within the mixing portion for creating a pressure differential within the testing channel.

In another embodiment, the analyzing portion may include an optical chamber to receive at least a portion of the aliquot for optical measurement of the fluid sample. In another embodiment, the mixing portion may be configured to allow the aliquot to mix with a reagent within the mixing portion. In yet another embodiment the reagent may be immobilized within the mixing portion.

In another aspect of the preset invention, a method for testing at least one fluid sample for LAL-reactive substances is provided. The method includes providing a microfluidic cartridge, wherein the cartridge includes at least two testing modules, wherein each testing module includes an inlet port for receiving one of the fluid samples, and at least four testing channels in fluid communication with the inlet port. Each of the testing channels may include a metering portion for metering an aliquot of the fluid sample, an analyzing portion, and a mixing portion. A valve may be positioned between the metering portion and the analyzing portion to selectively fluidly separate the metering portion from the analyzing portion. The method may further include introducing at least one fluid sample into at least one of the inlet ports. The method also includes introducing the microfluidic cartridge into an optical reader for optically measuring at least one fluid sample in the microfluidic cartridge. The method further includes performing a testing process on each of sample in the microfluidic cartridge and recording measurement data from the testing process.

In another embodiment, the method may further comprise motivating each of the aliquots from the metering portion to the analyzing portion for optical measurement in the analyzing portion of each testing channel. In yet another embodiment, a vacuum, centrifugal forces, or pneumatic pressure may motivate the flow of the aliquot across said valve from the metering portion to the analyzing portion. In another embodiment, each testing module may include at least one pressure port to which the vacuum or pneumatic pressure may be applied to create a pressure differential within the testing modules to motivate the flow of the aliquots.

In yet another method embodiment, the fluid sample may be introduced to the inlet ports manually or in an automated manner.

In another aspect of the preset invention, a method for testing at least one fluid sample for LAL-reactive substances is provided. The method includes providing a microfluidic cartridge, wherein the cartridge includes at least two testing modules, wherein each testing module includes an inlet port for receiving one of the fluid samples, and at least four testing channels in fluid communication with the inlet port. Each of the testing channels may include a metering portion for metering an aliquot of the fluid sample, an analyzing portion, and a mixing portion. A valve may be positioned between the metering portion and the analyzing portion to selectively fluidly separate the metering portion from the analyzing portion. The method may further include introducing at least one fluid sample into at least one of the inlet ports. The method further includes performing a testing process on each of sample in the microfluidic cartridge and recording measurement data from the testing process. In another method, the microfluidic cartridge may be introduced into an optical reader before introducing the fluid sample into an inlet port. In another method, the fluid sample may be mixed with a reagent during the testing process. In yet another embodiment, the reagent may be immobilized within the mixing portion.

In another aspect of the present invention, the measurement data may comprise aliquot volumes, reaction kinetics, fluid motions, transmission, absorption, optical density, color, color value, hue, spectrum, turbidity, scattered light, chemiluminescence, fluorescence, and magnetic resonance. The testing process and measurement data may be validated using historical data and/or data from known reaction kinetics. In yet another embodiment, a tracer may be immobilized within the mixing portion and/or the analyzing portion to aid in measuring the aliquot volume.

While embodiments of the present invention have been described, it should be understood that the present invention is not so limited and modifications may be made without departing from the present invention. The scope of the present invention is defined by the appended claims, and all devices, processes, and methods that come within the meaning of the claims, either literally or by equivalence, are intended to be embraced therein.

What is claimed is:

1. A microfluidic cartridge for testing fluid samples comprising at least two (2) testing modules, wherein:

each testing module includes at least one inlet port for receiving one of said fluid samples, and at least four (4) testing channels in fluid communication with said inlet port;

each of said testing channels includes a metering portion for metering an aliquot of said fluid sample, an analyzing portion, and a mixing portion, said metering portion fluidly communicates with said analyzing portion, and said analyzing portion fluidly communicates with said mixing portion, wherein a valve is positioned between said metering portion and said analyzing portion to selectively fluidly separate said metering portion from said analyzing portion; and wherein:

each testing module has at least one testing channel with at least one reagent isolated therein, said reagent comprising a *Limulus amebocyte lysate* (LAL)-reactive substance.

2. The microfluidic cartridge of claim 1, wherein at least one testing module is a calibration module comprising at least eight (8) testing channels and wherein: at least two (2) of said testing channels have no LAL-reactive substance therein; at least two (2) of said testing channels have a first amount of a LAL reactive substance isolated therein; at least two (2) of said testing channels have a second amount of a LAL reactive substance isolated therein; and at least two (2) of said testing channels have a third amount of a LAL reactive substance isolated therein.

3. The microfluidic cartridge of claim 1, wherein at least one testing module is a sample measurement module comprising at least four (4) testing channels and wherein; at least two (2) of said testing channels have no LAL reactive substance therein; and at least two (2) of said testing channels have a spike with an amount of a LAL reactive-substance isolated therein.

4. The microfluidic cartridge of claim 1, wherein all of said testing channels have at least one additional reagent isolated therein, said additional reagent comprising a detection reagent.

5. The microfluidic cartridge of claim 1 further comprising an exit port in fluid communication with said inlet port for removing excess of said fluid sample.

6. The microfluidic cartridge of claim 1, wherein said valve is configured to allow vacuum, centrifugal forces, or pneumatic pressure to motivate said aliquot to flow across said valve from said metering portion to said analyzing portion.

7. The microfluidic cartridge of claim 1 further comprising a first pressure port positioned within said metering portion and adjacent to an end of said analyzing portion for creating a pressure differential within said testing channel.

8. The microfluidic cartridge of claim 7 further comprising a second pressure port positioned within said mixing portion for creating a pressure differential within said testing channel.

9. The microfluidic cartridge of claim 1, wherein said analyzing portion includes an optical chamber to receive at least a portion of said aliquot for optical measurement of said fluid sample.

10. The microfluidic cartridge of claim 1, wherein said mixing portion is configured to allow said aliquot to mix with said reagent within said mixing portion.

11. The microfluidic cartridge of claim 1, wherein said reagent is immobilized within said mixing portion.

12. The microfluidic cartridge of claim 1, wherein said analyzing portion is positioned between said metering portion and said mixing portion;

wherein a volume of said mixing portion is greater than a volume of said metering portion.

13. A method for testing at least one fluid sample for *Limulus amebocyte lysate* (LAL)-reactive substances, said method comprising:

using a microfluidic cartridge, said microfluidic cartridge comprising at least two (2) testing modules, wherein:

each testing module includes at least one inlet port for receiving one of said fluid samples, and at least four (4) testing channels in fluid communication with said inlet port; and each of said testing channels includes a metering portion for metering an aliquot of said fluid sample, an analyzing portion, and a mixing portion, said metering portion fluidly communicates with said analyzing portion, and said analyzing portion fluidly communicates with said mixing portion, wherein a valve is positioned between said metering portion and said analyzing portion to selectively fluidly separate said metering portion from said analyzing portion;

wherein said microfluidic cartridge contains a reagent for detecting said LAL-reactive substances;

introducing said at least one fluid sample into at least one of said inlet ports;

performing a testing process for said LAL-reactive substances on each of said at least one fluid sample in said microfluidic cartridge; and recording measurement data from said testing process.

14. The method of claim 13 further comprising motivating flow of each of said aliquots from said metering portions to said analyzing portions for optical measurement in said analyzing portion of each testing channel.

15. The method of claim 14, wherein a vacuum, centrifugal forces, or pneumatic pressure motivates flow of said aliquot across said valve from said metering portion to said analyzing portion.

16. The method of claim 15, wherein each of said testing modules includes at least one pressure port to which said vacuum or pneumatic pressure is applied to create a pressure differential within said testing modules to motivate flow of said aliquots.

17. The method of claim 13, wherein introducing said at least one fluid sample into at least one of said inlet ports includes manually introducing said at least one fluid sample or introducing said at least one fluid sample in an automated manner.

18. The method of claim 13 further comprising the step of introducing said microfluidic cartridge into an optical reader before introducing said at least one sample fluid into one of said inlet ports.

19. The method of claim 13, wherein said fluid sample is mixed with said reagent during said testing process.

20. The method of claim 13, wherein said reagent is immobilized within said mixing portion.

21. The method of claim 13, wherein said measurement data comprises, aliquot volumes, reaction kinetics, fluid motions, transmission, absorption, optical density, color, color value, hue, spectrum, turbidity, scattered light, chemiluminescence, fluorescence, and magnetic resonance.

22. The method of claim 21, wherein said testing process and measurement data are validated using historical measurement data and/or data from known reaction kinetics.

23. The method of claim 22, wherein a tracer is immobilized within said mixing portion and/or said analyzing portion to aid in measuring and validating said fluid motions and/or said aliquot volume.

24. The method of claim 13, wherein said analyzing portion is positioned between said metering portion and said mixing portion;

wherein a volume of said mixing portion is greater than a volume of said metering portion.

* * * * *